(12) United States Patent
Hale et al.

(10) Patent No.: US 7,581,540 B2
(45) Date of Patent: Sep. 1, 2009

(54) AEROSOL DRUG DELIVERY DEVICE INCORPORATING PERCUSSIVELY ACTIVATED HEAT PACKAGES

(75) Inventors: Ron L. Hale, Woodside, CA (US); Mingzu Lei, Mountain View, CA (US); Peter M. Lloyd, Walnut Creek, CA (US); Patrik Munzar, Belmont, CA (US); Krishnamohan Sharma, Santa Clara, CA (US); Dennis W. Solas, San Francisco, CA (US); Matthew D. Stracker, Vacaville, CA (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 1055 days.

(21) Appl. No.: 10/917,720

(22) Filed: Aug. 12, 2004

(65) Prior Publication Data

US 2006/0032501 A1 Feb. 16, 2006

(51) Int. Cl.
*A61M 16/00* (2006.01)
*H05B 3/00* (2006.01)
*A62B 7/00* (2006.01)
*F24J 3/00* (2006.01)

(52) U.S. Cl. .............................. 128/203.27; 128/204.17

(58) Field of Classification Search ................. 514/343, 514/169, 953, 957, 965, 492–505; 424/443, 424/40–42; 131/194, 195, 270–273; 128/200.14, 128/200.24, 202.21, 203.12, 203.14, 203.15, 128/203.17, 203.26, 203.27, 204.13, 204.17; 222/330; 126/263
See application file for complete search history.

(56) References Cited

U.S. PATENT DOCUMENTS

| 802,256 | A | 10/1905 | Bamberger et al. |
|---|---|---|---|
| 1,239,634 | A | 9/1917 | Stuart |
| 1,535,486 | A | 4/1925 | Lundy |
| 1,803,334 | A | 5/1931 | Lehmann |
| 1,864,980 | A | 6/1932 | Curran |

(Continued)

FOREIGN PATENT DOCUMENTS

CA 2152684 1/1996

(Continued)

OTHER PUBLICATIONS

U.S. Appl. No. 10/057,198, Office Action mailed Jan. 26, 2007.

(Continued)

*Primary Examiner*—Justine R Yu
*Assistant Examiner*—Kristen C Matter
(74) *Attorney, Agent, or Firm*—Swanson & Bratschun, L.L.C.

(57) ABSTRACT

Aerosol drug delivery devices incorporating percussively activated heat packages are disclosed. The heat packages include a percussive igniter and a fuel capable of undergoing an exothermic oxidation-reduction reaction when ignited by the percussive igniter. The drug delivery devices disclosed can be activated by an actuation mechanism to vaporize a thin solid film comprising a drug disposed on the exterior of a hat package. Metal coordination complexes of volatile drugs, and in particular nicotine, from which the drug can be selectively vaporized when heated are also disclosed. The use of aerosol drug delivery devices comprising thin films of nicotine metal salt complexes for the treatment of nicotine craving and for effecting smoking cessation are also disclosed.

52 Claims, 11 Drawing Sheets

U.S. PATENT DOCUMENTS

Figure 1:
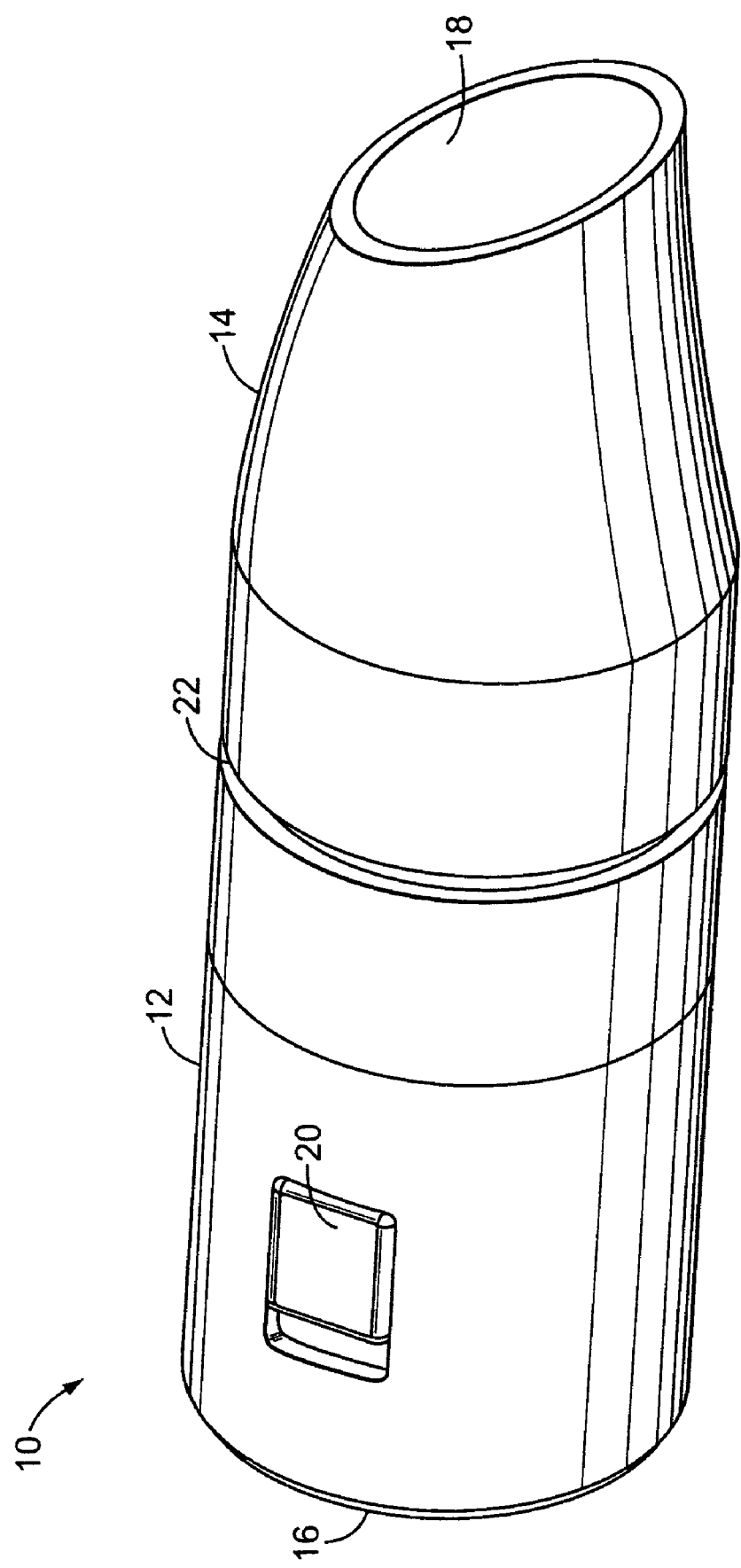

| | | | |
|---|---|---|---|
| 2,024,225 A | 12/1935 | Igari | |
| 2,084,299 A | 6/1937 | Borden | |
| 2,086,140 A | 7/1937 | Ernst | |
| 2,230,753 A | 2/1941 | Klavehn et al. | |
| 2,230,754 A | 2/1941 | Klavehn et al. | |
| 2,243,669 A | 5/1941 | Clyne | |
| 2,280,598 A | 4/1942 | Meridith | |
| 2,309,846 A | 2/1943 | Einar | |
| 2,469,656 A | 5/1949 | Lienert | |
| 2,500,790 A | 3/1950 | Bennett | |
| 2,531,548 A | 11/1950 | Bennett | |
| 2,624,332 A | 1/1953 | Lang | |
| 2,714,649 A | 8/1955 | Critzer | |
| 2,741,812 A | 4/1956 | Andre | |
| 2,761,055 A | 8/1956 | Ike | |
| 2,887,106 A | 5/1959 | Robinson | |
| 2,898,649 A | 8/1959 | Murray | |
| 2,902,484 A | 9/1959 | Horclois | |
| 2,906,094 A | 9/1959 | Damon et al. | |
| 2,953,443 A | 9/1960 | Lloyd | |
| 2,999,460 A | 9/1961 | Stinger et al. | |
| 3,043,977 A | 7/1962 | Morowitz | |
| 3,080,624 A | 3/1963 | Webber, III | |
| 3,118,798 A | 1/1964 | Winkler | |
| 3,150,020 A | 9/1964 | Kilmer | |
| 3,160,097 A | 12/1964 | Colburn, Jr. et al. | |
| 3,164,600 A | 1/1965 | Janssen et al. | |
| 3,169,095 A | 2/1965 | Thiel et al. | |
| 3,200,819 A | 8/1965 | Gilbert | |
| 3,219,533 A | 11/1965 | Mullins | |
| 3,238,076 A | 3/1966 | Taylor et al. | |
| 3,282,729 A | 11/1966 | Richardson et al. | |
| 3,296,249 A | 1/1967 | Bell | |
| 3,299,185 A | 1/1967 | Oda et al. | |
| 3,311,459 A | 3/1967 | Francis et al. | |
| 3,363,559 A | 1/1968 | Estes | |
| 3,371,085 A | 2/1968 | Reeder et al. | |
| 3,393,197 A | 7/1968 | Pachter | |
| 3,433,791 A | 3/1969 | Bentley et al. | |
| 3,503,814 A | 3/1970 | Helms, Jr. et al. | |
| 3,535,063 A | 10/1970 | Anderson et al. | |
| 3,560,607 A | 2/1971 | Hartley et al. | |
| 3,575,714 A | 4/1971 | Bennett et al. | |
| 3,580,250 A * | 5/1971 | Oroza | 128/202.26 |
| 3,695,179 A | 10/1972 | Rainone et al. | |
| 3,701,782 A | 10/1972 | Hester | |
| 3,703,144 A | 11/1972 | Colburn, Jr. | |
| 3,724,990 A | 4/1973 | Schupp | |
| 3,724,991 A | 4/1973 | Schupp | |
| 3,730,669 A | 5/1973 | Shaffer | |
| 3,749,547 A | 7/1973 | Gregory et al. | |
| 3,763,347 A | 10/1973 | Whitaker et al. | |
| 3,791,302 A | 2/1974 | McLeod | |
| 3,792,302 A | 2/1974 | Downing et al. | |
| 3,828,676 A | 8/1974 | Junker | |
| 3,830,671 A | 8/1974 | McArdle | |
| 3,831,606 A | 8/1974 | Damani | |
| 3,847,650 A | 11/1974 | Gregory et al. | |
| 3,864,326 A | 2/1975 | Babington | |
| 3,893,798 A | 7/1975 | Sterling | |
| 3,894,040 A | 7/1975 | Buzby, Jr. | |
| 3,909,463 A | 9/1975 | Hartman | |
| 3,930,796 A | 1/1976 | Haensel | |
| 3,943,941 A | 3/1976 | Boyd et al. | |
| 3,949,743 A | 4/1976 | Shanbrom | |
| 3,971,377 A | 7/1976 | Damani | |
| 3,982,095 A | 9/1976 | Robinson | |
| 3,987,052 A | 10/1976 | Hester, Jr. | |
| 4,000,022 A | 12/1976 | Beckert et al. | |
| 4,008,723 A | 2/1977 | Borthwick et al. | |
| 4,013,061 A * | 3/1977 | Trumble et al. | 44/250 |
| 4,020,379 A | 4/1977 | Manning | |
| 4,025,285 A | 5/1977 | Brown | |
| 4,045,156 A | 8/1977 | Chu et al. | |
| 4,047,483 A | 9/1977 | Williams | |
| 4,053,337 A | 10/1977 | Collins | |
| 4,059,388 A | 11/1977 | Shaffer | |
| 4,078,881 A | 3/1978 | Anderson et al. | |
| 4,079,742 A | 3/1978 | Rainer et al. | |
| 4,096,549 A | 6/1978 | Anderson et al. | |
| 4,104,210 A | 8/1978 | Coran et al. | |
| 4,121,583 A | 10/1978 | Chen | |
| 4,130,082 A | 12/1978 | Bouchard et al. | |
| 4,141,369 A | 2/1979 | Burruss | |
| 4,158,084 A | 6/1979 | Prentice | |
| 4,160,765 A | 7/1979 | Weinstock | |
| 4,166,087 A | 8/1979 | Cline et al. | |
| 4,183,912 A | 1/1980 | Rosenthale | |
| 4,184,099 A | 1/1980 | Lindauer et al. | |
| 4,190,654 A | 2/1980 | Gherardi et al. | |
| 4,193,388 A | 3/1980 | Yang | |
| 4,198,200 A | 4/1980 | Fonda et al. | |
| RE30,285 E | 5/1980 | Babington | |
| 4,205,673 A | 6/1980 | Wise | |
| 4,205,758 A | 6/1980 | Wise et al. | |
| 4,219,031 A | 8/1980 | Rainer et al. | |
| 4,229,447 A | 10/1980 | Porter | |
| 4,229,931 A | 10/1980 | Schlueter et al. | |
| 4,232,002 A | 11/1980 | Nogrady | |
| 4,236,544 A | 12/1980 | Osaka | |
| 4,251,525 A | 2/1981 | Weinstock | |
| 4,276,243 A | 6/1981 | Partus | |
| 4,280,629 A | 7/1981 | Slaughter | |
| 4,284,089 A | 8/1981 | Ray | |
| 4,286,604 A | 9/1981 | Ehretsmann et al. | |
| 4,303,083 A | 12/1981 | Burruss, Jr. | |
| 4,329,924 A | 5/1982 | Lagofun | |
| 4,340,072 A | 7/1982 | Bolt et al. | |
| 4,346,059 A | 8/1982 | Spector | |
| 4,347,855 A | 9/1982 | Lanzillotti et al. | |
| 4,354,432 A | 10/1982 | Cannavo et al. | |
| 4,372,210 A | 2/1983 | Shaffer et al. | |
| 4,372,213 A | 2/1983 | Rozner et al. | |
| 4,374,686 A | 2/1983 | Davitt et al. | |
| 4,376,767 A | 3/1983 | Sloan | |
| 4,391,285 A | 7/1983 | Burnett et al. | |
| 4,419,153 A | 12/1983 | Boberg | |
| 4,423,071 A | 12/1983 | Chignac et al. | |
| 4,474,191 A | 10/1984 | Steiner | |
| 4,484,576 A | 11/1984 | Albarda | |
| 4,484,960 A | 11/1984 | Rucker | |
| 4,508,726 A | 4/1985 | Coleman | |
| 4,523,589 A | 6/1985 | Krauser | |
| 4,526,758 A | 7/1985 | Alengoz et al. | |
| 4,556,539 A | 12/1985 | Spector | |
| 4,566,451 A | 1/1986 | Badewien | |
| 4,588,425 A | 5/1986 | Usry et al. | |
| 4,588,721 A | 5/1986 | Mahan | |
| 4,591,615 A | 5/1986 | Aldred et al. | |
| 4,605,552 A | 8/1986 | Fritschi | |
| 4,627,963 A | 12/1986 | Olson | |
| 4,647,428 A | 3/1987 | Gyulay | |
| 4,647,433 A | 3/1987 | Spector | |
| 4,654,370 A | 3/1987 | Marriott, III et al. | |
| 4,671,270 A * | 6/1987 | Kato | 128/202.26 |
| 4,683,231 A | 7/1987 | Glassman | |
| 4,693,868 A | 9/1987 | Katsuda et al. | |
| 4,700,629 A | 10/1987 | Benson et al. | |
| 4,708,151 A | 11/1987 | Shelar | |
| 4,714,082 A | 12/1987 | Banerjee et al. | |
| 4,721,224 A | 1/1988 | Kawabata | |
| 4,722,334 A | 2/1988 | Blackmer et al. | |
| 4,734,560 A | 3/1988 | Bowen | |
| 4,735,217 A | 4/1988 | Gerth et al. | |

| | | | | | |
|---|---|---|---|---|---|
| 4,735,358 A | 4/1988 | Osamo et al. | 5,186,164 A | 2/1993 | Raghuprasad |
| 4,753,758 A | 6/1988 | Miller | 5,192,548 A | 3/1993 | Velasquez et al. |
| 4,755,508 A | 7/1988 | Bock et al. | 5,224,498 A | 7/1993 | Deevi et al. |
| 4,756,318 A | 7/1988 | Clearman et al. | 5,229,120 A | 7/1993 | DeVincent |
| 4,757,764 A | 7/1988 | Thureson et al. | 5,229,382 A | 7/1993 | Chakrabarti et al. |
| 4,765,347 A | 8/1988 | Sensabaugh, Jr. et al. | 5,240,922 A | 8/1993 | O'Neill |
| 4,771,795 A | 9/1988 | White et al. | 5,249,586 A | 10/1993 | Morgan et al. |
| 4,774,971 A | 10/1988 | Vieten | 5,255,674 A | 10/1993 | Oftedal et al. |
| 4,793,365 A | 12/1988 | Sensabaugh, Jr. et al. | 5,261,424 A | 11/1993 | Sprin et al. |
| 4,793,366 A | 12/1988 | Hill | 5,264,433 A | 11/1993 | Sato et al. |
| 4,800,903 A | 1/1989 | Ray et al. | 5,284,133 A | 2/1994 | Burns et al. |
| 4,801,411 A | 1/1989 | Wellinghoff et al. | 5,285,798 A | 2/1994 | Banerjee et al. |
| 4,814,161 A | 3/1989 | Jinks et al. | 5,292,499 A | 3/1994 | Evans et al. |
| 4,819,665 A | 4/1989 | Roberts et al. | 5,322,018 A | 6/1994 | Hadden et al. |
| 4,848,374 A | 7/1989 | Chard et al. | 5,322,075 A | 6/1994 | Deevi et al. |
| 4,852,561 A | 8/1989 | Sperry | 5,333,106 A | 7/1994 | Lanpher et al. |
| 4,853,052 A | 8/1989 | Calsson et al. | 5,345,951 A | 9/1994 | Serrano et al. |
| 4,853,517 A | 8/1989 | Bowen et al. | 5,357,984 A | 10/1994 | Farrier et al. |
| 4,854,331 A | 8/1989 | Banerjee et al. | 5,363,842 A | 11/1994 | Mishelevich et al. |
| 4,858,630 A | 8/1989 | Banerjee et al. | 5,364,838 A | 11/1994 | Rubsamen |
| 4,863,720 A | 9/1989 | Burghart et al. | 5,366,770 A | 11/1994 | Wang |
| 4,881,541 A | 11/1989 | Eger et al. | 5,372,148 A | 12/1994 | McCafferty et al. |
| 4,881,556 A | 11/1989 | Clearman et al. | 5,376,386 A | 12/1994 | Ganderton et al. |
| 4,889,850 A | 12/1989 | Thornfeldt et al. | 5,388,574 A | 2/1995 | Ingebrethsen |
| 4,892,037 A | 1/1990 | Betts | 5,391,081 A | 2/1995 | Lampotang et al. |
| 4,892,109 A | 1/1990 | Strubel | 5,399,574 A | 3/1995 | Robertson et al. |
| 4,895,719 A | 1/1990 | Radhakrishnan et al. | 5,400,808 A | 3/1995 | Turner et al. |
| 4,906,417 A | 3/1990 | Gentry | 5,431,167 A | 7/1995 | Savord |
| 4,911,157 A | 3/1990 | Miller | 5,436,230 A | 7/1995 | Soudant et al. |
| 4,917,119 A | 4/1990 | Potter et al. | 5,445,606 A | 8/1995 | Haak et al. |
| 4,917,120 A | 4/1990 | Hill | 5,451,408 A | 9/1995 | Mezei et al. |
| 4,917,830 A | 4/1990 | Ortiz et al. | 5,454,363 A | 10/1995 | Sata |
| 4,922,901 A | 5/1990 | Brooks et al. | 5,456,247 A | 10/1995 | Shilling et al. |
| 4,924,883 A | 5/1990 | Perfetti et al. | 5,456,677 A | 10/1995 | Spector |
| 4,928,714 A | 5/1990 | Shannon | 5,457,100 A | 10/1995 | Daniel |
| 4,941,483 A | 7/1990 | Ridings et al. | 5,457,101 A | 10/1995 | Greenwood et al. |
| 4,947,874 A | 8/1990 | Brooks et al. | 5,459,137 A | 10/1995 | Andrasi et al. |
| 4,947,875 A | 8/1990 | Brooks et al. | 5,462,740 A | 10/1995 | Evenstad et al. |
| 4,963,289 A | 10/1990 | Ortiz et al. | 5,468,936 A | 11/1995 | Deevi et al. |
| 4,984,158 A | 1/1991 | Hillsman | 5,479,919 A | 1/1996 | Buchtal |
| 4,989,619 A | 2/1991 | Clearman et al. | 5,501,236 A | 3/1996 | Hill et al. |
| 5,016,425 A | 5/1991 | Weick | 5,507,277 A | 4/1996 | Rubsamen et al. |
| 5,017,575 A | 5/1991 | Golwyn | 5,509,354 A | 4/1996 | Dorffler et al. |
| 5,019,122 A | 5/1991 | Clearman et al. | 5,511,726 A | 4/1996 | Greenspan et al. |
| 5,020,548 A | 6/1991 | Farrier et al. | 5,519,019 A | 5/1996 | Andrasi et al. |
| 5,027,707 A | 7/1991 | Mei | 5,522,385 A | 6/1996 | Lloyd et al. |
| 5,027,836 A | 7/1991 | Shannon et al. | 5,525,329 A | 6/1996 | Snyder et al. |
| 5,033,483 A | 7/1991 | Clearman et al. | 5,538,020 A | 7/1996 | Farrier et al. |
| 5,042,509 A | 8/1991 | Banerjee et al. | 5,543,434 A | 8/1996 | Weg |
| 5,049,389 A | 9/1991 | Radhakrishnan | 5,544,646 A | 8/1996 | Lloyd et al. |
| 5,060,666 A | 10/1991 | Clearman et al. | 5,549,849 A | 8/1996 | Namura et al. |
| 5,060,667 A | 10/1991 | Strubel | 5,564,442 A | 10/1996 | MacDonald et al. |
| 5,060,671 A | 10/1991 | Counts et al. | 5,573,565 A | 11/1996 | Dalton et al. |
| 5,067,499 A | 11/1991 | Banerjee et al. | 5,584,701 A | 12/1996 | Lampotang et al. |
| 5,072,726 A | 12/1991 | Mazloomdoost et al. | 5,586,550 A | 12/1996 | Ivri et al. |
| 5,076,292 A | 12/1991 | Sensabaugh, Jr. et al. | 5,591,368 A | 1/1997 | Fleischhauer et al. |
| 5,099,861 A * | 3/1992 | Clearman et al. ............ 131/194 | 5,592,934 A | 1/1997 | Thwaites |
| 5,109,180 A | 4/1992 | Boultinghouse et al. | 5,593,792 A | 1/1997 | Farrier et al. |
| 5,112,598 A | 5/1992 | Biesalski | 5,605,146 A | 2/1997 | Sarela |
| 5,118,494 A | 6/1992 | Schultz et al. | 5,605,897 A | 2/1997 | Beasley, Jr. et al. |
| 5,119,834 A | 6/1992 | Shannon et al. | 5,607,691 A | 3/1997 | Hale et al. |
| 5,126,123 A | 6/1992 | Johnson | 5,619,984 A | 4/1997 | Hodson et al. |
| 5,133,368 A | 7/1992 | Neumann et al. | 5,622,944 A | 4/1997 | Hale et al. |
| 5,135,009 A | 8/1992 | Muller et al. | 5,623,115 A | 4/1997 | Lauritzen et al. |
| 5,137,034 A | 8/1992 | Perfetti et al. | 5,626,360 A | 5/1997 | Lauritzen et al. |
| 5,144,962 A | 9/1992 | Counts et al. | 5,627,178 A | 5/1997 | Chakrabarti et al. |
| 5,146,915 A | 9/1992 | Montgomery | 5,641,938 A | 6/1997 | Holland et al. |
| 5,156,170 A | 10/1992 | Clearman et al. | 5,649,554 A | 7/1997 | Sprinkel |
| 5,160,664 A | 11/1992 | Liu | 5,654,520 A | 8/1997 | Boberg et al. |
| 5,164,740 A | 11/1992 | Ivri | 5,655,523 A | 8/1997 | Hodson et al. |
| 5,166,202 A | 11/1992 | Schweizer | 5,656,255 A | 8/1997 | Jones |
| 5,167,242 A | 12/1992 | Turner et al. | 5,660,166 A | 8/1997 | Lloyd et al. |
| 5,177,071 A | 1/1993 | Freidinger et al. | 5,660,413 A | 8/1997 | Bergerson et al. |

| Patent No. | Date | Name |
|---|---|---|
| 5,666,977 A | 9/1997 | Higgins et al. |
| 5,672,843 A | 9/1997 | Evans et al. |
| 5,686,691 A | 11/1997 | Hamilton et al. |
| 5,690,809 A | 11/1997 | Subramaniam et al. |
| 5,694,919 A | 12/1997 | Rubsamen et al. |
| 5,697,896 A | 12/1997 | McNichols et al. |
| 5,718,222 A | 2/1998 | Lloyd et al. |
| 5,724,957 A | 3/1998 | Rubsamen et al. |
| 5,725,756 A | 3/1998 | Subramaniam et al. |
| 5,733,572 A | 3/1998 | Unger et al. |
| 5,735,263 A | 4/1998 | Rubsamen et al. |
| 5,738,865 A | 4/1998 | Baichwal et al. |
| 5,743,250 A | 4/1998 | Gonda et al. |
| 5,743,251 A | 4/1998 | Howell et al. |
| 5,744,469 A | 4/1998 | Tran |
| 5,747,001 A | 5/1998 | Wiedmann et al. |
| 5,756,449 A | 5/1998 | Andersen et al. |
| 5,758,637 A | 6/1998 | Ivri et al. |
| 5,763,813 A | 6/1998 | Cohen et al. |
| 5,767,117 A | 6/1998 | Moskowitz et al. |
| 5,769,621 A | 6/1998 | Early et al. |
| 5,770,222 A | 6/1998 | Unger et al. |
| 5,771,882 A | 6/1998 | Psaros et al. |
| 5,776,928 A | 7/1998 | Beasley, Jr. |
| 5,804,212 A | 9/1998 | Illum |
| 5,809,997 A | 9/1998 | Wolf |
| 5,817,656 A | 10/1998 | Beasley, Jr. et al. |
| 5,819,756 A | 10/1998 | Mielordt |
| 5,823,178 A | 10/1998 | Lloyd et al. |
| 5,829,436 A | 11/1998 | Rubsamen et al. |
| 5,833,891 A | 11/1998 | Subramaniam et al. |
| 5,840,246 A | 11/1998 | Hammons et al. |
| 5,845,933 A | 12/1998 | Walker et al. |
| 5,855,564 A | 1/1999 | Ruskewicz |
| 5,855,913 A | 1/1999 | Hanes et al. |
| 5,874,064 A | 2/1999 | Edwards et al. |
| 5,874,481 A | 2/1999 | Weers et al. |
| 5,875,776 A | 3/1999 | Vaghefi |
| 5,878,752 A | 3/1999 | Adams et al. |
| 5,884,620 A | 3/1999 | Gonda et al. |
| 5,890,908 A | 4/1999 | Lampotang et al. |
| 5,894,841 A | 4/1999 | Voges |
| 5,900,249 A | 5/1999 | Smith |
| 5,906,811 A | 5/1999 | Hersh |
| 5,907,075 A | 5/1999 | Subramaniam et al. |
| 5,910,301 A | 6/1999 | Farr et al. |
| 5,915,378 A | 6/1999 | Lloyd et al. |
| 5,918,595 A | 7/1999 | Olsson |
| 5,928,520 A | 7/1999 | Haumesser |
| 5,929,093 A | 7/1999 | Pang et al. |
| 5,934,272 A | 8/1999 | Lloyd et al. |
| 5,934,289 A | 8/1999 | Watkins et al. |
| 5,935,604 A | 8/1999 | Illum |
| 5,938,117 A | 8/1999 | Ivri |
| 5,939,100 A | 8/1999 | Albrechtsen et al. |
| 5,941,240 A | 8/1999 | Gonda et al. |
| 5,944,012 A | 8/1999 | Pera |
| 5,957,124 A | 9/1999 | Lloyd et al. |
| 5,960,792 A | 10/1999 | Lloyd et al. |
| 5,970,973 A | 10/1999 | Gonda et al. |
| 5,971,951 A | 10/1999 | Ruskewicz |
| 5,985,309 A | 11/1999 | Edwards et al. |
| 5,993,805 A | 11/1999 | Sutton et al. |
| 6,004,970 A | 12/1999 | O'Malley et al. |
| 6,008,214 A | 12/1999 | Kwon et al. |
| 6,008,216 A | 12/1999 | Chakrabarti et al. |
| 6,013,050 A | 1/2000 | Bellhouse et al. |
| 6,014,969 A | 1/2000 | Lloyd et al. |
| 6,014,970 A | 1/2000 | Ivri et al. |
| 6,014,972 A | 1/2000 | Sladek |
| 6,041,777 A | 3/2000 | Faithfull et al. |
| 6,044,777 A | 4/2000 | Walsh |
| 6,048,550 A | 4/2000 | Chan et al. |
| 6,048,857 A | 4/2000 | Ellinwood, Jr. et al. |
| 6,050,260 A | 4/2000 | Daniell et al. |
| 6,051,257 A | 4/2000 | Kodas et al. |
| 6,051,566 A | 4/2000 | Bianco |
| 6,062,210 A | 5/2000 | Welles |
| RE36,744 E | 6/2000 | Goldberg |
| 6,080,248 A | 6/2000 | Finck et al. |
| 6,089,857 A | 7/2000 | Matsuura et al. |
| 6,090,212 A | 7/2000 | Mahawili |
| 6,095,134 A | 8/2000 | Sievers et al. |
| 6,095,153 A | 8/2000 | Kessler et al. |
| 6,102,036 A | 8/2000 | Slutsky et al. |
| 6,113,795 A | 9/2000 | Subramaniam et al. |
| 6,117,866 A | 9/2000 | Bondinell et al. |
| 6,125,853 A | 10/2000 | Susa et al. |
| 6,126,919 A | 10/2000 | Stefely et al. |
| 6,131,566 A | 10/2000 | Ashurst et al. |
| 6,131,570 A | 10/2000 | Schuster et al. |
| 6,133,327 A | 10/2000 | Kimura et al. |
| 6,135,369 A | 10/2000 | Prendergast et al. |
| 6,155,268 A | 12/2000 | Takeuchi |
| 6,168,661 B1 | 1/2001 | Dinkelman |
| 6,211,171 B1 | 4/2001 | Sawynok et al. |
| 6,234,167 B1 | 5/2001 | Cox et al. |
| 6,241,969 B1 | 6/2001 | Saidi et al. |
| 6,250,289 B1 | 6/2001 | Gonda et al. |
| 6,255,334 B1 | 7/2001 | Sands |
| 6,263,872 B1 | 7/2001 | Schuster et al. |
| 6,264,922 B1 | 7/2001 | Wood et al. |
| 6,267,110 B1 | 7/2001 | Tenenboum et al. |
| 6,284,287 B1 | 9/2001 | Sarlikiotis et al. |
| 6,289,813 B1 | 9/2001 | Duguet et al. |
| 6,289,889 B1 | 9/2001 | Bell et al. |
| 6,290,986 B1 | 9/2001 | Murdock et al. |
| 6,299,900 B1 | 10/2001 | Reed et al. |
| 6,300,710 B1 | 10/2001 | Nakamori |
| 6,306,431 B1 | 10/2001 | Zhang et al. |
| 6,313,176 B1 | 11/2001 | Ellinwood, Jr. et al. |
| 6,324,979 B1 | 12/2001 | Troianello |
| 6,352,506 B1 | 3/2002 | Eppstein et al. |
| 6,376,550 B1 | 4/2002 | Raber et al. |
| 6,391,282 B1 | 5/2002 | Dugger, III |
| 6,408,854 B1 | 6/2002 | Gonda et al. |
| 6,413,930 B1 | 7/2002 | Ratti et al. |
| 6,420,351 B1 | 7/2002 | Tsai et al. |
| 6,431,166 B2 | 8/2002 | Gonda et al. |
| 6,443,152 B1 | 9/2002 | Lockhart et al. |
| 6,444,326 B1 | 9/2002 | Smith |
| 6,444,665 B1 | 9/2002 | Helton et al. |
| 6,461,591 B1 | 10/2002 | Keller et al. |
| 6,478,903 B1 | 11/2002 | John, Jr. et al. |
| 6,479,074 B2 | 11/2002 | Murdock et al. |
| 6,487,971 B1 | 12/2002 | Anderson |
| 6,491,233 B2 | 12/2002 | Nichols |
| 6,497,780 B1 | 12/2002 | Carlson |
| 6,506,454 B2 | 1/2003 | Ishigami |
| 6,506,762 B1 | 1/2003 | Horvath et al. |
| 6,514,482 B1 | 2/2003 | Bartus et al. |
| 6,516,796 B1 | 2/2003 | Cox et al. |
| 6,557,552 B1 | 5/2003 | Cox et al. |
| 6,568,390 B2 | 5/2003 | Nichols et al. |
| 6,591,839 B2 | 7/2003 | Meyer et al. |
| 6,632,047 B2 | 10/2003 | Vinegar et al. |
| 6,638,981 B2 | 10/2003 | Williams et al. |
| 6,682,716 B2 | 1/2004 | Hodges et al. |
| 6,701,922 B2 | 3/2004 | Hindle et al. |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |

| | | | | | | |
|---|---|---|---|---|---|---|
| 6,740,309 B2 | 5/2004 | Rabinowitz et al. | | 2002/0031480 A1 | 3/2002 | Peart et al. |
| 6,743,415 B2 | 6/2004 | Rabinowitz et al. | | 2002/0035945 A1 | 3/2002 | Knowlton et al. |
| 6,759,029 B2 | 7/2004 | Hale et al. | | 2002/0037437 A1 | 3/2002 | Yamamoto |
| 6,772,756 B2 | 8/2004 | Shayan | | 2002/0037828 A1 | 3/2002 | Wilson et al. |
| 6,772,757 B2 | 8/2004 | Sprinkel, Jr. et al. | | 2002/0058009 A1 | 5/2002 | Bartus et al. |
| 6,776,978 B2 | 8/2004 | Rabinowitz et al. | | 2002/0061281 A1 | 5/2002 | Osbakken et al. |
| 6,779,520 B2 | 8/2004 | Genova et al. | | 2002/0078946 A1 | 6/2002 | Sprinkel, Jr. et al. |
| 6,780,399 B2 | 8/2004 | Rabinowitz et al. | | 2002/0078955 A1 | 6/2002 | Nichols et al. |
| 6,780,400 B2 | 8/2004 | Rabinowitz et al. | | 2002/0086852 A1 | 7/2002 | Cantor |
| 6,783,753 B2 | 8/2004 | Rabinowitz et al. | | 2002/0097139 A1 | 7/2002 | Gerber et al. |
| 6,797,259 B2 | 9/2004 | Rabinowitz et al. | | 2002/0112723 A1 | 8/2002 | Schuster et al. |
| 6,803,031 B2 | 10/2004 | Rabinowitz et al. | | 2002/0117175 A1 | 8/2002 | Kottayil et al. |
| 6,805,853 B2 | 10/2004 | Rabinowitz et al. | | 2002/0176841 A1 | 11/2002 | Barker et al. |
| 6,805,854 B2 | 10/2004 | Hale et al. | | 2003/0004142 A1 | 1/2003 | Prior et al. |
| 6,814,954 B2 | 11/2004 | Rabinowitz et al. | | 2003/0015196 A1 | 1/2003 | Hodges et al. |
| 6,814,955 B2 | 11/2004 | Rabinowitz et al. | | 2003/0015197 A1 | 1/2003 | Hale et al. |
| 6,855,310 B2 | 2/2005 | Rabinowitz et al. | | 2003/0032638 A1 | 2/2003 | Kim et al. |
| 6,884,408 B2 | 4/2005 | Rabinowitz et al. | | 2003/0037437 A1 | 2/2003 | Das et al. |
| 6,993,811 B2 | 2/2006 | Das et al. | | 2003/0051728 A1 | 3/2003 | Lloyd et al. |
| 6,994,843 B2 | 2/2006 | Rabinowitz et al. | | 2003/0062042 A1 | 4/2003 | Wensley et al. |
| 7,005,121 B2 | 2/2006 | Rabinowitz et al. | | 2003/0070738 A1 | 4/2003 | Hamilton |
| 7,005,122 B2 | 2/2006 | Hale et al. | | 2003/0106551 A1 | 6/2003 | Sprinkel |
| 7,008,615 B2 | 3/2006 | Rabinowitz et al. | | 2003/0118512 A1 | 6/2003 | Shen |
| 7,008,616 B2 | 3/2006 | Rabinowitz et al. | | 2003/0131843 A1 | 7/2003 | Lu |
| 7,011,819 B2 | 3/2006 | Hale et al. | | 2003/0138508 A1 | 7/2003 | Novack et al. |
| 7,011,820 B2 | 3/2006 | Rabinowitz et al. | | 2003/0209240 A1 | 11/2003 | Hale et al. |
| 7,014,840 B2 | 3/2006 | Hale et al. | | 2004/0009128 A1 | 1/2004 | Rabinowitz et al. |
| 7,014,841 B2 | 3/2006 | Rabinowitz et al. | | 2004/0016427 A1 | 1/2004 | Byron et al. |
| 7,018,619 B2 | 3/2006 | Rabinowitz et al. | | 2004/0083919 A1 | 5/2004 | Hosey et al. |
| 7,018,620 B2 | 3/2006 | Rabinowitz et al. | | 2004/0096402 A1 | 5/2004 | Hodges et al. |
| 7,018,621 B2 | 3/2006 | Hale et al. | | 2004/0099266 A1 | 5/2004 | Cross et al. |
| 7,022,312 B2 | 4/2006 | Rabinowitz et al. | | 2004/0101481 A1 | 5/2004 | Hale et al. |
| 7,029,658 B2 | 4/2006 | Rabinowitz et al. | | 2004/0102434 A1 | 5/2004 | Hale et al. |
| 7,033,575 B2 | 4/2006 | Rabinowitz et al. | | 2004/0105818 A1 | 6/2004 | Every et al. |
| 7,040,314 B2 | 5/2006 | Nguyen et al. | | 2004/0105819 A1 | 6/2004 | Hale et al. |
| 7,045,118 B2 | 5/2006 | Rabinowitz et al. | | 2004/0162517 A1 | 8/2004 | Furst et al. |
| 7,045,119 B2 | 5/2006 | Rabinowitz et al. | | 2004/0234699 A1 | 11/2004 | Hale et al. |
| 7,048,909 B2 | 5/2006 | Rabinowitz et al. | | 2004/0234914 A1 | 11/2004 | Hale et al. |
| 7,052,679 B2 | 5/2006 | Rabinowitz et al. | | 2004/0234916 A1 | 11/2004 | Hale et al. |
| 7,052,680 B2 | 5/2006 | Rabinowitz et al. | | 2005/0000711 A1* | 1/2005 | Huristone et al. .............. 173/19 |
| 7,060,254 B2 | 6/2006 | Rabinowitz et al. | | 2005/0016550 A1 | 1/2005 | Katase |
| 7,060,255 B2 | 6/2006 | Rabinowitz et al. | | 2005/0034723 A1 | 2/2005 | Bennett et al. |
| 7,063,830 B2 | 6/2006 | Rabinowitz et al. | | 2005/0037506 A1 | 2/2005 | Hale et al. |
| 7,063,831 B2 | 6/2006 | Rabinowitz et al. | | 2005/0079166 A1 | 4/2005 | Damani et al. |
| 7,063,832 B2 | 6/2006 | Rabinowitz et al. | | 2005/0126562 A1 | 6/2005 | Rabinowitz et al. |
| 7,067,114 B2 | 6/2006 | Rabinowitz et al. | | 2005/0131739 A1 | 6/2005 | Rabinowitz et al. |
| 7,070,761 B2 | 7/2006 | Rabinowitz et al. | | 2005/0268911 A1 | 12/2005 | Cross et al. |
| 7,070,762 B2 | 7/2006 | Rabinowitz et al. | | 2006/0032496 A1 | 2/2006 | Hale et al. |
| 7,070,763 B2 | 7/2006 | Rabinowitz et al. | | 2006/0032501 A1 | 2/2006 | Hale et al. |
| 7,070,764 B2 | 7/2006 | Rabinowitz et al. | | 2006/0120962 A1 | 6/2006 | Rabinowitz et al. |
| 7,070,765 B2 | 7/2006 | Rabinowitz et al. | | 2006/0153779 A1 | 7/2006 | Rabinowitz et al. |
| 7,070,766 B2 | 7/2006 | Rabinowitz et al. | | 2006/0177382 A1 | 8/2006 | Rabinowitz et al. |
| 7,078,016 B2 | 7/2006 | Rabinowitz et al. | | 2006/0193788 A1 | 8/2006 | Hale et al. |
| 7,078,017 B2 | 7/2006 | Rabinowitz et al. | | 2006/0216243 A1 | 9/2006 | Rabinowitz et al. |
| 7,078,018 B2 | 7/2006 | Rabinowitz et al. | | 2006/0216244 A1 | 9/2006 | Rabinowitz et al. |
| 7,078,019 B2 | 7/2006 | Rabinowitz et al. | | 2006/0233717 A1 | 10/2006 | Hale et al. |
| 7,078,020 B2 | 7/2006 | Rabinowitz et al. | | 2006/0233718 A1 | 10/2006 | Rabinowitz et al. |
| 7,087,216 B2 | 8/2006 | Rabinowitz et al. | | 2006/0233719 A1 | 10/2006 | Rabinowitz et al. |
| 7,087,217 B2 | 8/2006 | Rabinowitz et al. | | 2006/0239936 A1 | 10/2006 | Rabinowitz et al. |
| 7,087,218 B2 | 8/2006 | Rabinowitz et al. | | 2006/0246011 A1 | 11/2006 | Rabinowitz et al. |
| 7,090,830 B2 | 8/2006 | Hale et al. | | 2006/0246012 A1 | 11/2006 | Rabinowitz et al. |
| 7,094,392 B2 | 8/2006 | Rabinowitz et al. | | 2006/0247573 A1 | 11/2006 | Alexandre et al. |
| 7,108,847 B2 | 9/2006 | Rabinowitz et al. | | 2006/0251587 A1 | 11/2006 | Rabinowitz et al. |
| 7,115,250 B2 | 10/2006 | Rabinowitz et al. | | 2006/0251588 A1 | 11/2006 | Rabinowitz et al. |
| 7,131,599 B2 | 11/2006 | Katase | | 2006/0257328 A1 | 11/2006 | Rabinowitz et al. |
| 7,169,378 B2 | 1/2007 | Rabinowitz et al. | | 2006/0257329 A1 | 11/2006 | Rabinowitz et al. |
| 7,229,966 B2 | 6/2007 | Quay et al. | | 2006/0269486 A1 | 11/2006 | Rabinowitz et al. |
| 7,402,777 B2 | 7/2008 | Hale et al. | | 2006/0269487 A1 | 11/2006 | Rabinowitz et al. |
| 2001/0020147 A1 | 9/2001 | Staniforth et al. | | 2006/0280692 A1 | 12/2006 | Rabinowitz et al. |
| 2001/0037104 A1 | 11/2001 | Zhang et al. | | 2006/0286042 A1 | 12/2006 | Rabinowitz et al. |
| 2001/0039262 A1 | 11/2001 | Venkataraman | | 2006/0286043 A1 | 12/2006 | Rabinowitz et al. |
| 2001/0042546 A1 | 11/2001 | Umeda et al. | | 2007/0014737 A1 | 1/2007 | Rabinowitz et al. |
| 2002/0000225 A1 | 1/2002 | Schuler et al. | | 2007/0028916 A1 | 2/2007 | Hale et al. |

| | | | | | | |
|---|---|---|---|---|---|---|
| 2007/0031340 | A1 | 2/2007 | Hale et al. | WO | WO 94/27576 | 12/1994 |
| 2007/0122353 | A1 | 5/2007 | Hale et al. | WO | WO 94/27653 | 12/1994 |
| 2007/0140982 | A1 | 6/2007 | Every et al. | WO | WO 95/31182 | 11/1995 |
| 2007/0178052 | A1 | 8/2007 | Rabinowitz et al. | WO | WO 96/00069 | 1/1996 |
| 2007/0286816 | A1 | 12/2007 | Hale et al. | WO | WO 96/00070 | 1/1996 |
| 2008/0110872 | A1 | 5/2008 | Hale et al. | WO | WO 96/00071 | 1/1996 |
| 2008/0175796 | A1 | 7/2008 | Rabinowitz et al. | WO | WO 96/09846 | 4/1996 |
| 2008/0216828 | A1 | 9/2008 | Wensley | WO | WO 96/10663 | 4/1996 |

FOREIGN PATENT DOCUMENTS

| | | |
|---|---|---|
| WO | WO 96/13161 | 5/1996 |
| WO | WO 96/13290 | 5/1996 |
| CN | 1082365 | 2/1994 |
| WO | WO 96/13291 | 5/1996 |
| CN | 1176075 | 3/1998 |
| WO | WO 96/13292 | 5/1996 |
| DE | 571 289 | 2/1933 |
| WO | WO 96/30068 | 10/1996 |
| DE | 26 48 308 | 4/1978 |
| WO | WO 96/31198 | 10/1996 |
| DE | 35 42 447 | 6/1987 |
| WO | WO 96/37198 | 11/1996 |
| DE | 195 46 341 | 1/1997 |
| WO | WO 97/16181 | 5/1997 |
| DE | 196 16 627 | 11/1997 |
| WO | WO 97/17948 | 5/1997 |
| DE | 198 54 007 | 5/2000 |
| WO | WO 97/23221 | 7/1997 |
| EP | 0 039 369 | 11/1981 |
| WO | WO 97/27804 | 8/1997 |
| EP | 0 244 837 | 11/1987 |
| WO | WO 97/31691 | 9/1997 |
| EP | 0 274 431 | 7/1988 |
| WO | WO 97/35562 | 10/1997 |
| EP | 0 277 519 | 8/1988 |
| WO | WO 97/35582 | 10/1997 |
| EP | 0 279 796 | 8/1988 |
| WO | WO 97/36574 | 10/1997 |
| EP | 0 358 114 | 3/1990 |
| WO | WO 97/40819 | 11/1997 |
| EP | 0 363 494 | 4/1990 |
| WO | WO 97/49690 | 12/1997 |
| EP | 0 430 559 | 6/1991 |
| WO | WO 98/02186 | 1/1998 |
| EP | 0 492 485 | 7/1992 |
| WO | WO 98/16205 | 4/1998 |
| EP | 0 606 486 | 7/1994 |
| WO | WO 98/22170 | 5/1998 |
| EP | 1 325 761 | 10/1995 |
| WO | WO 98/29110 | 7/1998 |
| EP | 0 734 719 | 2/1996 |
| WO | WO 98/31346 | 7/1998 |
| EP | 0 780 659 | 6/1997 |
| WO | WO 98/34595 | 8/1998 |
| EP | 0 816 674 A1 | 1/1998 |
| WO | WO 98/36651 | 8/1998 |
| EP | 0 936 205 | 8/1999 |
| WO | WO 98/37896 | 9/1998 |
| EP | 0 967 214 | 12/1999 |
| WO | WO 99/04797 | 2/1999 |
| EP | 1 065 296 | 1/2001 |
| WO | WO 99/16419 | 4/1999 |
| EP | 1 079 002 | 2/2001 |
| WO | WO 99/24433 | 5/1999 |
| EP | 1 080 720 | 3/2001 |
| WO | WO 99/37347 | 7/1999 |
| EP | 1 177 793 | 2/2002 |
| WO | WO 99/37625 | 7/1999 |
| EP | 0 808 635 B1 | 7/2003 |
| WO | WO 99/44664 | 9/1999 |
| EP | 1 345 268 A2 | 9/2003 |
| WO | WO 99/55362 | 11/1999 |
| FR | 921 852 A | 5/1947 |
| WO | WO 99/59710 | 11/1999 |
| FR | 1 289 468 | 4/1962 |
| WO | WO 99/64094 | 12/1999 |
| FR | 2 234 532 | 1/1975 |
| WO | WO 00/00176 | 1/2000 |
| FR | 2 428 068 A | 1/1980 |
| WO | WO 00/00215 | 1/2000 |
| FR | 2 506 927 | 12/1982 |
| WO | WO 00/00244 | 1/2000 |
| GB | 502 761 | 1/1938 |
| WO | WO 00/19991 | 4/2000 |
| GB | 903 866 | 8/1962 |
| WO | WO 00/27359 | 5/2000 |
| GB | 1 001 901 | 8/1965 |
| WO | WO 00/27363 | 5/2000 |
| GB | 1 366 041 | 9/1974 |
| WO | WO 00/28979 | 5/2000 |
| GB | 2 049 651 | 12/1980 |
| WO | WO 00/29053 | 5/2000 |
| GB | 2 108 390 | 5/1983 |
| WO | WO 00/29167 | 5/2000 |
| GB | 2 122 903 | 1/1984 |
| WO | WO 00/35417 | 6/2000 |
| GB | 2 123 948 | 2/1984 |
| WO | WO 00/38618 | 7/2000 |
| HU | 200105 B | 10/1988 |
| WO | WO 00/44350 | 8/2000 |
| HU | 2193292 | 6/1993 |
| WO | WO 00/44730 | 8/2000 |
| JP | 57 078968 | 5/1982 |
| WO | WO 00/47203 | 9/2000 |
| WO | WO 85/00520 | 2/1985 |
| WO | WO 00/51491 | 9/2000 |
| WO | WO 88/08304 | 11/1988 |
| WO | WO 00/64940 | 11/2000 |
| WO | WO 90/02737 | 3/1990 |
| WO | WO 00/66084 | 11/2000 |
| WO | WO 90/07333 | 7/1990 |
| WO | WO 00/66106 | 11/2000 |
| WO | WO 91/07947 | 6/1991 |
| WO | WO 00/66206 | 11/2000 |
| WO | WO 91/18525 | 12/1991 |
| WO | WO 00/72827 | 12/2000 |
| WO | WO 92/05781 | 4/1992 |
| WO | WO 00/76673 | 12/2000 |
| WO | WO 92/15353 | 9/1992 |
| WO | WO 01/05459 | 1/2001 |
| WO | WO 92/19303 | 11/1992 |
| WO | WO 01/13957 | 3/2001 |
| WO | WO 93/12823 | 7/1993 |
| WO | WO 01/17568 | 3/2001 |
| WO | WO 94/09842 | 5/1994 |
| WO | WO 01/19528 | 3/2001 |
| WO | WO 94/16717 | 8/1994 |
| WO | WO 01/29011 | 4/2001 |
| WO | WO 94/16757 | 8/1994 |
| WO | WO 01/32144 | 5/2001 |
| WO | WO 94/16759 | 8/1994 |
| WO | WO 01/41732 | 6/2001 |
| WO | WO 94/17369 | 8/1994 |
| WO | WO 01/69136 | 9/2001 |
| WO | WO 94/17370 | 8/1994 |
| WO | WO 01/95903 | 12/2001 |
| WO | | | WO | WO 02/00198 | 1/2002 |

| | | |
|---|---|---|
| WO | WO 02/24158 | 3/2002 |
| WO | WO 02/056866 | 7/2002 |
| WO | WO 02/083119 | 10/2002 |
| WO | WO 02/094242 | 11/2002 |
| WO | WO 02/098389 | 12/2002 |
| WO | WO 02/102297 | 12/2002 |
| WO | WO 03/021158 | 3/2003 |
| WO | WO 03/024456 | 3/2003 |
| WO | WO 03/037412 | 5/2003 |
| WO | WO 03/095012 | 11/2003 |
| WO | WO 2004/011396 | 2/2004 |
| WO | WO 2004/050139 | 6/2004 |
| WO | WO 2004/054551 | 7/2004 |
| WO | WO 2004/104490 | 12/2004 |
| WO | WO 2004/104491 | 12/2004 |
| WO | WO 2004/104492 | 12/2004 |
| WO | WO 2004/104493 | 12/2004 |
| WO | WO 2004/106268 | 12/2004 |

OTHER PUBLICATIONS

U.S. Appl. No. 10/057,198, Office Action mailed Jul. 3, 2006.
U.S. Appl. No. 10/057,198, Office Action mailed Sep. 20, 2005.
U.S. Appl. No. 10/057,198, Office Action mailed Dec. 4, 2003.
U.S. Appl. No. 10/057,197, Office Action mailed Jan. 12, 2005.
U.S. Appl. No. 10/057,197, Office Action mailed Jun. 3, 2004.
U.S. Appl. No. 10/057,197, Office Action mailed Jun. 5, 2007.
Office Action mailed Sep. 21, 2006 with respect to U.S. Appl. No. 10/057,197.
Office Action mailed Dec. 15, 2003 with respect to U.S. Appl. No. 10/057,197.
Office Action mailed Feb. 27, 2004 with respect to U.S. Appl. No. 10/146,080.
Office Action mailed Mar. 20, 2007 with respect to U.S. Appl. No. 10/146,080.
Office Action mailed Jun. 5, 2006 with respect to U.S. Appl. No. 10/146,080.
Office Action mailed Aug. 25, 2005 with respect to U.S. Appl. No. 10/146,080.
Office Action mailed Dec. 28, 2007 with respect to U.S. Appl. No. 10/146,080.
Office Action mailed Feb. 12, 2007 with respect to U.S. Appl. No. 10/146,086.
Office Action mailed Oct. 30, 2007 with respect to U.S. Appl. No. 10/146,086.
Office Action mailed Dec. 13, 2005 with respect to U.S. Appl. No. 10/146,086.
Office Action mailed Feb. 16, 2007 with respect to U.S. Appl. No. 10/146,088.
Office Action mailed Sep. 28, 2007 with respect to U.S. Appl. No. 10/146,088.
Office Action mailed Nov. 21, 2007 with respect to U.S. Appl. No. 10/146,088.
Office Action mailed Aug. 13, 2003 with respect to U.S. Appl. No. 10/153,313.
Office Action mailed Mar. 8, 2005 with respect to U.S. Appl. No. 10/718,982.
Office Action mailed Jan. 22, 2007 with respect to U.S. Appl. No. 10/851,429.
Office Action mailed May 9, 2006 with respect to U.S. Appl. No. 10/851,429.
Office Action mailed Jan. 24, 2007 with respect to U.S. Appl. No. 10/851,883.
Office Action mailed May 10, 2006 with respect to U.S. Appl. No. 10/851,883.
Office Action mailed Jan. 30, 2007 with respect to U.S. Appl. No. 10/851,432.
Office Action mailed May 3, 2006 with respect to U.S. Appl. No. 10/851,432.
Anderson, M.E. (1982). "Recent Advances in Methodology and Concepts for Characterizing Inhalation Pharmacokinetic Parameters in Animals and Man," Drug Metabolism Reviews. 13(5):799-826.
Bennett, R. L. et al. (1981). "Patient-Controlled Analgesia: A New Concept of Postoperative Pain Relief," Annual Surg. 195(6):700-705.
Benowitz (1994). "Individual Differences in Nicotine Kinetics and Metabolism in Humans," NIDA Research Monography, 2 pages.
BP: Chemicals Products-Barrier Resins (1999). Located at <http://www.bp.com/chemicals/products/product.asp> (visited on Aug. 2, 2001), 8 pages.
Brand, P. et al. (Jun. 2000). "Total Deposition of Therapeutic Particles During Spontaneous and Controlled Inhalations," Journal of Pharmaceutical Sciences. 89(6):724-731.
Campbell, Fiona A. et al. (2001) "Are cannabinoids an effective and safe treatment option in the management of pain? A qualitative systemic review," BMJ, 323 pp. 1-6.
Carroll, M.E. et al. (1990), "Cocaine-Base Smoking in Rhesus Monkey: Reinforcing and Physiological Effects," Psychopharmacology (Berl) 102:443-450.
Cichewicz, Diana L. et al. (May 1999) "Enhancement of mu opioid antinociception by oral Delta 9—tetrahydrocannabinol: Dose response analysis and receptor identification" Journal of Pharmacology and Experimental Therapeutics vol. 289 (2): 859-867.
Clark, A. and Byron, P. (1986). "Dependence of Pulmonary Absorption Kinetics on Aerosol Particle Size," Z. Erkrank. 166:13-24.
Dallas, C. et al. (1983). "A Small Animal Model for Direct Respiratory and Hemodynamic Measurements in Toxicokinetic Studies of Volatile Chemicals," Devlopments in the Science and Practice of Toxicology. Hayes, A. W. et al. eds., Elsevier Science Publishers, New York. pp. 419-422.
Darquenne, C. et al. (1997). "Aerosol Dispersion in Human Lung: Comparison Between Numerical Simulations and Experiments for Bolus Tests," American Physiological Society. 966-974.
Database Biosis "Online!" Biosciences Information Service, Philadelphia, PA 1979, Knight, V. et al., "Amantadine aerosol in humans", database accession No. PREV 198069035552 abstract, & Antimicrobial Agents and Chemotherapy 16(5):572-578.
Database Biosis "Online!" Biosciences Information Service, Philadelphia, PA 1979, Wilson. S.Z. et al., "Amatadine Aerosol Particle A.erosol Generation and Delivery to Man" Database accession No. PREV198069008137, abstract & Proceedings of the Society for Experimental Biology and Medicine 161(3):350-354.
Database WPI, Section CH, Week 198941, Derwent Publications Ltd., London, GB; AN 1989-297792 AP002230849 & JP 01 221313 (Nippon Create 1(K), Sep. 4, 1989, abstract.
Davies, C. N. et al. (May 1972). "Breathing of Half-Micron Aerosols," Journal of Applied Physiology. 32(5):591-600.
Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.
Drugs Approved by the FDA—Drug Name: Nicotrol Inhaler (2000) located at <http://www.centerwatch.com/patient/drugs/dru202.html> (Visited on Aug. 2, 2001), 2 pages.
Feynman, R.P. et al. (1964). "Chapter 32: Refractive Index of Dense Materials" The Feyman Lectures on Physics: Mainly Electromagnetism and Matter. Addison-Wesley: Publishing Company, Inc., Reading, Massachusetts: pp. 32-1-32-13.
Finlay, W. H. (2001). "The Mechanics of Inhaled Pharmaceutical Aerosols", Academic Press: San Diego Formula 2.39. pp. 3-14 (Table of Contents). pp. v-viii.
Gleeson, et al. (1982) "Chlorpromazine Hyperalgesia Antagonizes Clonidine Analgesia, but Enhances Morphine Analgesia in Rats Tested in a Hot-Water Tail-Flick Paradigm" Psychopharmacology vol. 78: 141-146.
Gonda, I. (1991). "Particle Deposition in the Human Respiratory Tract," Chapter 176, The Lung: Scientific Foundations. Crystal R.G. and West, J.B. (eds.), Raven Publishers, New York. pp. 2289-2294.
Graves, D. A. et al. (1983). "Patient-Controlled Analgesia," Annals of Internal Medicine. 99:360-366.
Hamon, et al. (1987) "Opioid Receptors and Neuropeptides in the CNS in Rats Treated Chronically with Amoxapine and Amitriptyline" Neuropharmacology vol. 26 No. 6: 531-539.
Hatsukami D., et al. (May 1990) "A Method for Delivery of Precise Doses of Smoked Cocaine-Base to Human." Pharmacology Biochemistry & Behavior. 36(1):1-7.

Heyder, J. et al. (1986). "Deposition of Particles in the Human Respiratory Tract in the Size Range 0.005-15 µm," J. Aerosol Sci. 17(5):811-822.

Huizer, H. (1987). "Analytical Studies on Illicit Heron. V. Efficacy of Volitization During Heroin Smoking." Pharmaceutisch Weekblad Scientific Edition. 9(4):203-211.

Hurt, R. D., MD and Robertson, C. R., PhD, (Oct. 1998). "Prying Open the Door to the Tobacco Industry's Secrets About Nicotine: The Minnesota Tobacco Trial," JAMA 280(13):1173-1181.

Hwang, S. L. (Jun. 1999). "Artificial Nicotine Studied: R. J. Reynolds Seeks to Develop Drugs that Mimic Tobacco's Potent Effects on Brain," Wall Street Journal, 3 pages.

James, A.C. et al., (1991). "The Respiratory Tract Deposition Model Proposed by the ICRP Task Group," Radiation Protection Dosimetry, 38(1/3):159-165.

Kim, M. H. and Patel, D.V. (1994). "BOP As a Reagent for Mild and Efficient Preparation of Esters," Tet. Letters 35:5603-5606.

Kreith, Frank et al. "Boundary-Layer Fundamentals" Principles of Heat Transfer. Section 4.3: p. 236-242.

Krikorian et al. (1985) "Role of Thermal Dissociation in the Direct Gas-Liquid Chromatographic Determination of Amine Maleate Salts" Anal. Chem. 57(1):312-315.

Leaver, T.R. (Nov. 9, 1994) "Interim Defence Standard: Composition SR 58" Ministry of Defence. Vo. 13-159/Issue 1.

Lichtman, A. H. et al. (1996). "Inhalation Exposure to Volatilized Opioids Produces Antinociception in Mice," Journal of Pharmacology and Experimental Therapeutics. 279(1):69-76 XP-001118649.

Lichtman, A. H. et al. (2000). "Pharmacological Evaluation of Aerosolized Cannabinoids in Mice" European Journal of Pharmacology, vol. 399, No. 2-3: 141-149.

Lopez, K. (Jul. 1999). "UK Researcher Develops Nicotinic Drugs with R. J. Reynolds," located at <http://www.eurekalert.org/pub_releases/1999-07/UoKM-Urdn-260799.php> (visited on Oct. 1, 2002), 1 page.

Love, C.M. "Development of a Titanium/Boron Blending Process." p. 37-44.

Lynch, Mary E. (2001) "Antidepressants as analgesics: a review of randomized controlled trials" J. Psychiatry Neuroscience vol. 26: 30-36.

Magnusson et al. (2000) "The Involvement of Dopamine in Nociception: the role of D1 and D2 Receptors in the Dorsolateral Striatum." Brain Research vol. 855: 260-266.

Martin, B. R. and Lue, L. P. (May/Jun. 1989). "Pyrolysis and Volatilization of Cocaine," Journal of Analytical Toxicology 13:158-162.

Mattox, A.J. and Carroll, M.E. (1996). "Smoked Heroin Self-Administration in Rhesus Monkeys," Psychopharmacology 125:195-201.

McCarthy, D.K., et al. (May 1985) "Burn Front Velocity as a function of Pellet Density in Iron/Potassium Perchlorate Heat Powders" Sandia Report.

McCormick, A.S.M., et al., "Bronchospasm During Inhalation of Nebulized Midazolam," British Journal of Anesthesia, vol. 80 (4), Apr. 1988, pp. 564-565 XP001119488.

McGee et al. (1979) "Phenotiazine Analgesia—Fact or Fantasy?" American Journal of Hospital Pharmacy vol. 36: 633-640.

Meng, Y. et al. (1997). "Inhalation Studies with Drugs of Abuse", NIDA Research Monogragh 173:201-224.

Meng, Y., et al. (1999). "Pharmacological effects of methamphetamine and other stimulants via inhalation exposure," Drug and Alcohol Dependence. 53:111-120.

Merzhanov, Alexander G., (Aug. 19, 1994) "Pyrotechnical Aspects of Self-Propogating High-Temperature Synthesis" Russian Academy of Sciences: International Pyrotechnics Seminar Colorado Springs, US Jul. 25-29, 1994.

Muralidharan et al. (1987) "Complexes of Cobalt (II), Nickel (II) & Copper (II) with Nicotine." Indian Journal of Chemistry 26A:348-349.

Pankow, J. (Mar. 2000). ACS Conference-San Francisco-Mar. 26, 2000. Chemistry of Tobacco Smoke. pp. 1-8.

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Perfetti (1983) "Structural study of nicotine salts" Beitraege zur Tabakforschung Internatioal 12(2):43-54.

Perfetti (2000) "The transfer of nicotine from nicotine salts to mainstream smoke" Beitraege zur Tabakforschung Internatioal 19(3):141-158.

Pfeiffer, Ronald (1982) "Drugs for pain in the elderly" Geriatrics vol. 37 No. 2: 67-76.

Poochikian, G. and Bertha, C.M. (2000). "Inhalation Drug Product Excipient Controls: Significance and Pitfalls," Resp. Drug Deliv. VII: 109-115.

Rapoport et al. (1997) CNS Drugs 7(1):37-46.

Riggs et al. (2001) "Thermochemical properties of nicotine salts" Beitraege zur Tabakforschung Internatioal 19(6):289-295.

Roux, Gillard M. "Laser Diode Ignition of the Combustion of Pyrotechnic Mixtures. Experimental study of the ignition of $Zr/KClO4$ and $Zr/PbCrO4$".

Schreiber et al. (1999) "The Atypical Neuroleptics Clozapine and Olanzapine Differ Regarding Their Antinociceptive Mechanisms and Potency" Pharmacology Biochemistry and Behavior vol. 64 No. 1: 75-80.

ScienceDaily Magazine, (Jul. 1999). "University of Kentucky Researcher Develops Nicotinic Drugs with R. J. Reynolds," located at <http://www.sciencedaily.com/releases/1999/07/990728073542.htm.> (visited on Sep. 23, 2002), 2 pages.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.

Streitwieser, A. and Heathcock, C. H. eds., (1981). Introduction to Organic Chemistry. Second edition, Macmillan Publishing Co., Inc., New York, pp. ix-xvi. (Table of Contents).

The Merck Index, 11th Ed. Contains information on fumaric and maleic acid and maleic anhydride.

Tsantilis, S. et al. (2001). "Sintering Time for Silica Particle Growth," Aerosol Science and Technology 34:237-246.

Vaportonics, Inc. (1998) located at http://www.vapotronics.com.au/banner.htm., 11 pages, (visited on Jun. 5, 2000).

Vaughan, N.P. (1990). "The Generation of Monodisperse Fibres of Caffeine" J. Aerosol Sci. 21(3): 453-462.

Ward, M. E. MD, et al. (Dec. 1997). "Morphine Pharmacokinetics after Pulmonary Administration from a Novel Aerosol Delivery System," Clinical Pharmocology & Therapeutics 62(6):596-609.

Williams, S. (Feb. 1999). "Rhone-Poulenc Rorer Inc. and Targacept Inc. Announce Alliance to Develop New Drugs to Treat Alzheimer's and Parkinson's Diseases"located at http://www.rpr.rpna.com/ABOUT_RPR/pressrels/1999/990209-targa.html (last visited on Jan. 28, 2000) 1 page.

Wood, R.W. et al. (1996). "Methylecgonidine Coats the Crack Particle." Pharmacology Biochemistry & Behavior. 53(1):57-66.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

U.S. Appl. No. 11/687,466, filed Mar. 16, 2007, Zaffaroni et al.
U.S. Appl. No. 11/964,630, filed Dec. 26, 2007, Hale et al.
U.S. Appl. No. 12/111,188, filed Apr. 28, 2008, Hale et al.
U.S. Appl. No. 12/117,737, filed May 8, 2008, Hale et al.
U.S. Appl. No. 12/211,247, filed Sep. 16, 2008, Sharma et al.
U.S. Appl. No. 12/211,554, filed Sep. 16, 2008, Sharma et al.
U.S. Appl. No. 12/211,628, filed Sep. 16, 2008, Lei et al.

De Yong et al. (1998) "Radiative Ignition of Pyrotechnics: Effect of Wavelength on Ignition Threshold" Propellants, Explosives, Pyrotechnics 23:328-332.

* cited by examiner

FIG. 7

FIG. 8

AEROSOL DRUG DELIVERY DEVICE INCORPORATING PERCUSSIVELY ACTIVATED HEAT PACKAGES

This disclosure relates to aerosol drug delivery devices incorporating percussively activated heat packages. The drug delivery devices can be activated by actuation mechanisms to vaporize thin films comprising a drug. These thin films can consist of a solid or a viscous liquid. This disclosure further relates to thin films comprising a metal coordination complex of a volatile compound in which the volatile compound is selectively vaporizable when heated. More particularly, this disclosure relates to thin films of nicotine metal salt complexes for the treatment of nicotine craving and for effecting smoking cessation.

Cigarette smoking provides an initial sharp rise in nicotine blood level as nicotine is absorbed through the lungs of a smoker. In general, a blood level peak produced by cigarettes of between 30-40 ng/mL is attained within 10 minutes of smoking. The rapid rise in nicotine blood level is postulated to be responsible for the postsynaptic effects at nicotinic cholinergic receptors in the central nervous system and at autonomic ganglia which induces the symptoms experienced by cigarette smokers, and may also be responsible for the craving symptoms associated with cessation of smoking.

While many nicotine replacement therapies have been developed, none of the therapies appear to reproduce the pharmacokinetic profile of the systemic nicotine blood concentration provided by cigarettes. As a consequence, conventional nicotine replacement therapies have not proven to be particularly effective in enabling persons to quit smoking. For example, many commercially available products for nicotine replacement in smoking cessation therapy are intended to provide a stable baseline concentration of nicotine in the blood. Nicotine chewing gum and transdermal nicotine patches are two examples of smoking cessation products which, while providing blood concentrations of nicotine similar to that provided by cigarettes at times greater than about 30 minutes, these products do not reproduce the sharp initial rise in blood nicotine concentrations obtained by smoking cigarettes. Nicotine gum is an ion-exchange resin that releases nicotine slowly when a patient chews, and the nicotine present in the mouth is delivered to the systemic circulation by buccal absorption. Nicotine patches provide a low, consistent blood level of nicotine to the user. Thus, both nicotine gum and transdermal nicotine do not reproduce the pharmacokinetic profile of nicotine blood levels obtained through cigarette smoking, and thus do not satisfy the craving symptoms experienced by many smokers when attempting to quit smoking.

Inhalation products which generate nicotine vapor are also ineffective as inhaled vapors are predominately absorbed through the tongue, mouth and throat, and are not deposited into the lungs. Smokeless nicotine products such as chewing tobacco, oral snuff or tobacco sachets deliver nicotine to the buccal mucosa where, as with nicotine gum, the released nicotine is absorbed only slowly and inefficiently. Nicotine blood levels from these products require approximately 30 minutes of use to attain a maximum nicotine blood concentration of approximately 12 ng/mL, which is less than half the peak value obtained from smoking one cigarette. Low nicotine blood levels obtained using a buccal absorption route may be due to first pass liver metabolism.

Orally administered formulations and lozenges are also relatively ineffective.

Rapid vaporization of thin films of drugs at temperatures up to 600° C. in less than 200 msec in an air flow can produce drug aerosols having high yield and high purity with minimal degradation of the drug. Condensation drug aerosols can be used for effective pulmonary delivery of drugs using inhalation medical devices. Devices and methods in which thin films of drugs deposited on metal substrates are vaporized by electrically resistive heating have been demonstrated. Chemically-based heat packages which can include a fuel capable of undergoing an exothermic metal oxidation-reduction reaction within an enclosure can also be used to produce a rapid thermal impulse capable of vaporizing thin films to produce high purity aerosols, as disclosed, for example in U.S. application Ser. No. 10/850,895 entitled "Self-Contained heating Unit and Drug-Supply Unit Employing Same" filed May 20, 2004, and U.S application Ser. No. 10/851,883, entitled "Percussively Ignited or Electrically Ignited Self-Contained Heating Unit and Drug Supply Unit Employing Same," filed May 20, 2004, the entirety of both of which are herein incorporated by reference. These devices and methods are appropriate for use with compounds that can be deposited as physically and chemically stable solids. Unless vaporized shortly after being deposited on the metal surface, liquids can evaporate or migrate from the surface. Therefore, while such devices can be used to vaporize liquids, the use of liquid drugs can impose certain undesirable complexity. Nicotine is a liquid at room temperature with a relatively high vapor pressure. Therefore, known devices and methods are not particularly suited for producing nicotine aerosols using the liquid drug.

Thus, there remains a need for a nicotine replacement therapy that provides a pharmacokinetic profile similar to that obtained by cigarette smoking, and thereby directly addresses the craving symptoms associated with the cessation of smoking.

Accordingly, a first aspect of the present disclosure provides a drug delivery device comprising a housing defining an airway, wherein the airway comprises at least one air inlet and a mouthpiece having at least one air outlet, at least one percussively activated heat package disposed within the airway, at least one drug disposed on the at least one percussively activated heat package, and a mechanism configured to impact the at least one percussively activated heat package. Drugs that can be coated as thin films (either solids or viscous liquids) are particularly suited for this aspect of the invention. Likewise, as discussed below, volatile or liquid drugs that can form a complex and then coated as a thin film are also suitable for use in this aspect of the invention. For purposed of clarity, "percussively activated heat package" herein means a heat package that has been configured so that it can be fired or activated by percussion. An "unactivated heat package" or "non-activated heat package" refers herein to a percussively activated heat package in a device, but one that is not yet positioned in the device so that it can be directly impacted and fired, although the heat package itself is configured to be activated by percussion when so positioned.

A second aspect of the present disclosure provides a percussively activated heat package comprising an enclosure comprising a region capable of being deformed by a mechanical impact, an anvil disposed within the enclosure, a percussive initiator composition disposed within the enclosure, wherein the initiator composition is configured to be ignited when the deformable region of the enclosure is deformed, and a fuel disposed within the enclosure configured to be ignited by the initiator composition.

A third aspect of the present disclosure provides metal coordination complexes comprising a volatile compound, and in particular metal coordination complexes of nicotine, wherein the compound is selectively vaporizable when heated.

A fourth aspect of the present disclosure provides a method of producing an aerosol of a compound by selectively vaporizing the compound from a thin film optionally comprising a metal coordination complex comprising the compound.

A fifth aspect of the present disclosure provides a method of delivering a drug to a patient comprising providing a drug delivery device comprising, a housing defining an airway, wherein the airway comprises at least one air inlet and a mouthpiece having at least one air outlet, at least two or more percussively activated heat package disposed within the airway, at least one drug disposed on the percussively activated heat packages, and a mechanism configured to impact the percussively activated heat packages, inhaling through the mouthpiece, and actuating the mechanism configured to impact, wherein the percussively activated heat package vaporizes the at least one drug to form an aerosol comprising the drug in the airway which is inhaled by the patient.

A sixth aspect of the present disclosure provides a method for treating nicotine craving and smoking cessation using a nicotine aerosol.

It is to be understood that both the foregoing general description and the following detailed description are exemplary and explanatory only and are not restrictive of certain embodiments, as claimed.

DESCRIPTION OF THE DRAWINGS

FIG. 1 is an isometric view of a drug delivery device according to certain embodiments.

FIG. 2 is a cross-sectional view of a drug delivery device incorporating percussively ignited heat packages according to certain embodiments.

FIG. 3 is a cross-sectional view of a heat package according to certain embodiments.

FIG. 4 is a cross-sectional view of a drug delivery device in which each heat package is disposed within a recess according to certain embodiments.

FIG. 5 is another view of heat packages disposed within recesses.

FIGS. 6A-6E illustrate additional embodiments of heat packages.

FIG. 7 shows a conceptual summary of the use of metal coordination complexes to stabilize volatile compounds, and subsequently selectively volatilize the organic compound from a solid thin film of the metal coordination complex.

Figure 8:
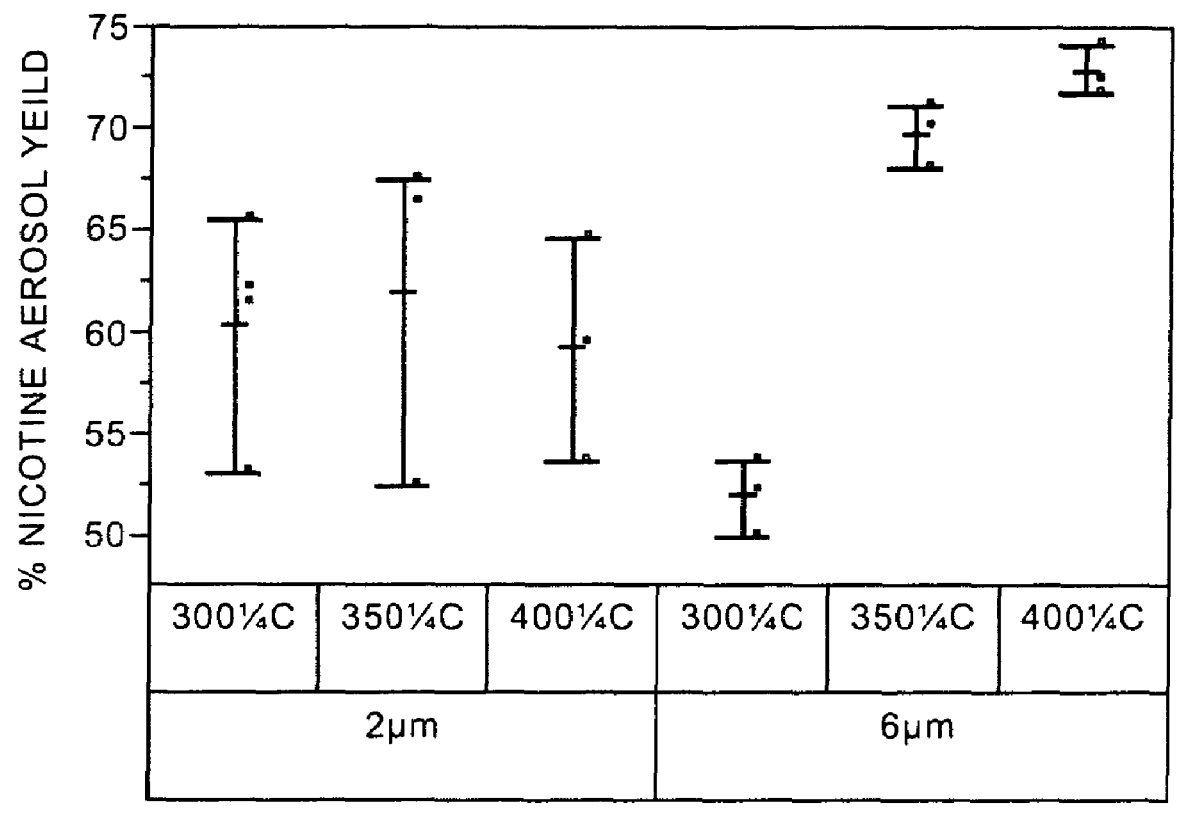

FIG. 8 is a chart showing percent nicotine aerosol yield of selectively volatilized solid thin films of a $(nicotine)_2$-$ZnBr_2$ metal coordination complex.

FIG. 9 is a chart showing percent nicotine aerosol purity of selectively volatilized solid thin films of a $(nicotine)_2$-$ZnBr_2$ metal coordination complex.

FIG. 10 is a view of a multidose heat packages as a reel for use in a drug delivery device.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

DESCRIPTION OF VARIOUS EMBODIMENTS

Unless otherwise indicated, all numbers expressing quantities and conditions, and so forth used in the specification and claims are to be understood as being modified in all instances by the term "about."

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit unless specifically stated otherwise.

Vaporization of thin films comprising a drug can be used for administering aerosols of a drug to a user. Inhalation drug delivery devices in which an aerosol is produced by vaporizing a solid thin film of a drug are described, for example, in U.S. patent application Ser. No. 10/850,895, the disclosure of which is incorporated herein by reference. In such devices, inhalation on the device by a patient activates a heating element on which is disposed a thin solid film of a drug. The fast thermal impulse vaporizes the drug which forms an aerosol in the air flow generated by the patient's inhalation. The aerosol is ingested by the patient and delivered to the patient's lung where the drug can be rapidly and efficiently absorbed into the patient's systemic circulation. Devices in which a fuel capable of undergoing an exothermic metal oxidation-reduction reaction to provide heat to vaporize a substance have also been described (see, for example, "Staccato Device Application." The thin films of metal coordination complexes of volatile compounds disclosed herein can be used in similar devices and in a similar manner to produce high purity drug aerosols.

It is postulated that treatment of nicotine craving and smoking cessation can be addressed by treatment regimens and/or therapies that reproduce the rapid onset of high nicotine blood concentrations achieved during cigarette smoking. A cigarette smoker typically inhales about 10 times over a period of about 5 minutes. Therefore, a nicotine delivery device capable of simulating the use profile of cigarette smoking would include from 5 to 20 doses of about 200 μg each of nicotine, which could then be intermittently released upon request by the user. While such protocols can be accommodated by previously described portable multi-dose drug delivery devices, for example, as disclosed in U.S. application Ser. No. 10/861,554, entitled "Multiple Dose Condensation Aerosol Devices and Methods of Forming Condensation Aerosols", filed Jun. 3, 2004 such devices employ electrically resistive heating to vaporize a thin solid film, and therefore require a relatively expensive and bulky power source such as a battery. Portable multi-dose drug delivery devices which do not incorporate batteries, which are readily disposable, and which are amenable to high volume, low cost manufacturing can be useful, particularly for nicotine replacement therapies. A mechanically actuated, percussively ignited, chemical heat package, can provide a compact, self-contained heating system capable of vaporizing thin films of drugs, for use in portable, multi-dose and single-dose drug delivery devices.

FIG. 1 shows an isometric view of a multi-dose drug delivery device incorporating a percussive heat package, and a mechanical actuation mechanism. A drug delivery device 10 includes a housing comprising an endpiece 12, and a mouthpiece 14. Endpiece 12 and mouthpiece 14 define an internal airway having at least one air inlet 16 (hidden), and at least one air outlet 18 defined by mouthpiece 14. A manually actuated push-button switch 20 is incorporated into endpiece 12. Endpiece 12 and mouthpiece 14 can be separate units that can be separably, rotatably, or fixedly connected at interface 22. The dimensions of drug delivery device 10 can be such that the device can be easily and ergonomically handled. For the purposes of nicotine replacement therapy, it can be useful that the look and feel of drug delivery device 10 simulate that of a cigarette, cigarillo or a cigar. For example, in certain embodiments, the length of endpiece 12 can be 1.4 inches with an outer diameter of 1.2 inches, and the length of mouthpiece 14 can be 1.8 inches to 2.5 inches. Mouthpiece 14 can have a diameter the same as that of endpiece 12 at interface 22, and can be tapered toward air outlet 18 as appropriate for user convenience and comfort, as well as to facilitate inhalation and delivery of a drug aerosol into the lungs of a user. The cross-sectional area of air outlet 18 can range from about 0.01 in$^2$ to about 1.5 in$^2$. The internal airway defined by endpiece 12 and mouthpiece 14 can accommodate an air flow rate typically produced during inhalation. For example, the airway defined by endpiece 12, and mouthpiece 14 can accommodate an air flow rate ranging from 10 L/min to 200 L/min. Endpiece 12 and mouthpiece 14 can be formed from a polymer or polymer composite, or from any other material capable of providing structural support for the internal components, including, for example, metals, alloys, composites, ceramics, and combinations thereof. The exterior surface of endpiece 12 and mouthpiece 14 can further be textured or include molded inserts to enhance the tactile and/or aesthetic qualities. The wall thickness of endpiece 12 and mouthpiece 14 can be any appropriate thickness that provides mechanical integrity to the delivery device and physical support for the internal components. In certain embodiments, endpiece 12 and mouthpiece 14 can be fabricated by injection molding methods using low cost plastics and/or plastic components.

Figure 2:
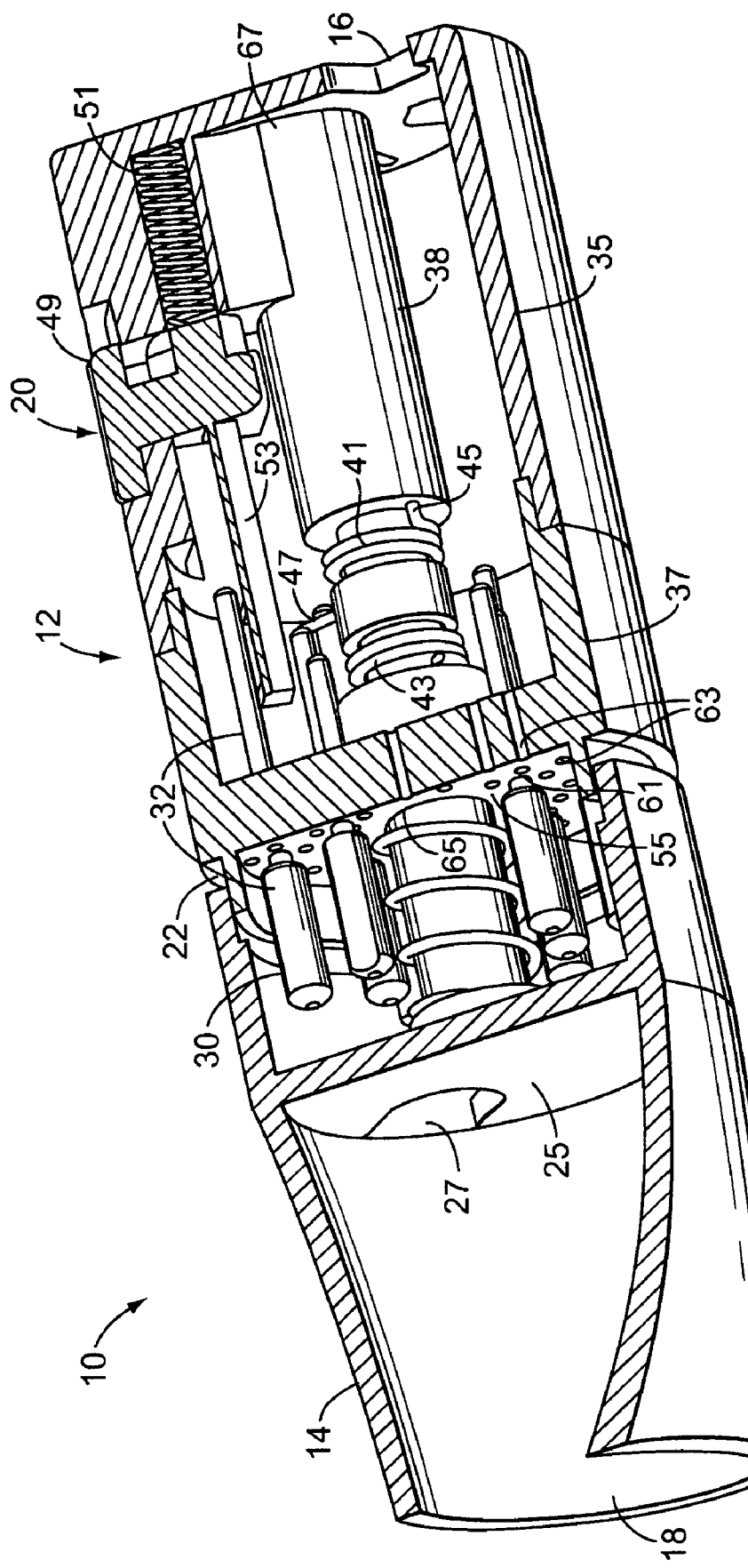

FIG. 2 shows a cut-away cross-sectional view of multi-dose drug delivery device 10. Mouthpiece 14 is slidably connected at interface 22 to endpiece 12, and as illustrated in FIG. 2, is pulled slightly apart from endpiece 12 in a partially disassembled configuration. Mouthpiece 14 includes an internal baffle 25 having a hole 27. In certain embodiments, the slidable connection at interface 22 can be used to rotate mouthpiece 14 with respect to endpiece 12 to orient hole 27 with respect to components retained within endpiece 12, and in particular, to align hole 27 with an individual heat package 32. Baffle 25 diverts air flowing in the airway through hole 27. When a patient inhales on mouthpiece 14, air enters air inlet 16, passes through plurality of holes 63, is diverted by baffle 25 through hole 27, and exits the device through air outlet 18.

To deliver a drug, such as nicotine to a user, a drug is vaporized from an exterior surface 30 of at least one heat package 32. A plurality of heat packages 32, for example from 5 to 30 heat packages are contained within each drug delivery device 10.

Figure 3:
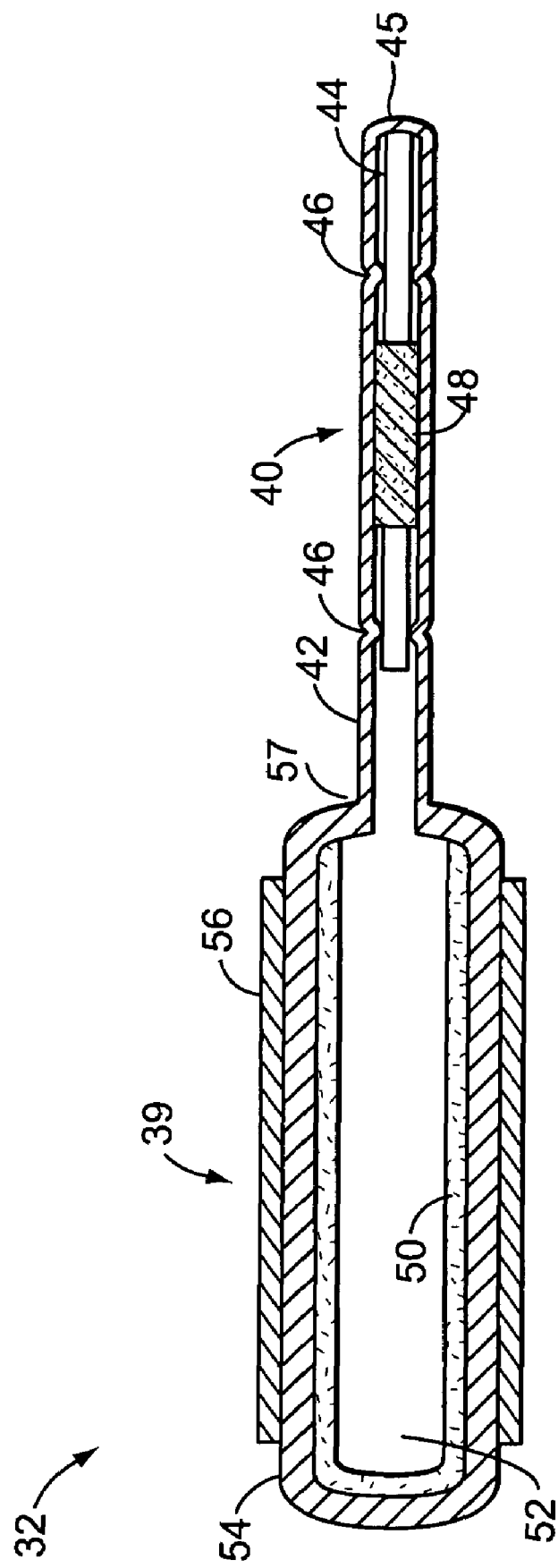

FIG. 3 shows a cross-sectional view of an embodiment of heat package 32. Each heat package 32 includes a percussive igniter 40 and a heating element 39. Percussive igniter 40 includes mechanically deformable tube 42, an anvil 44 coaxially disposed within deformable tube 42, and held in place by indentations 46. An initiator composition 48 is disposed on a region of anvil 44. When mechanically impacted with sufficient force, deformable tube 42 is deformed, compressing initiator composition 48 between deformable tube 42 and anvil 44 causing initiator composition 48 to deflagrate and eject sparks. The interior 52 of heating element 39 includes a fuel 50 capable of producing a rapid, high intensity heat impulse when ignited. Examples of appropriate fuels are disclosed herein. The exterior surface 54 of heating element 39 includes a thin film 56 of a drug or drug-containing composition. Deflagration of initiator composition 48 causes fuel 50 to ignite. The heat generated by burning fuel 50 heats exterior surface 54 of heating element 39. The thermal energy from exterior surface 54 is transferred to and vaporizes thin film 56 of drug or drug containing composition from exterior surface 54. The drug vapor can condense in the air flow in device 10 (see FIGS. 1-2) to form a drug aerosol.

Figure 4:
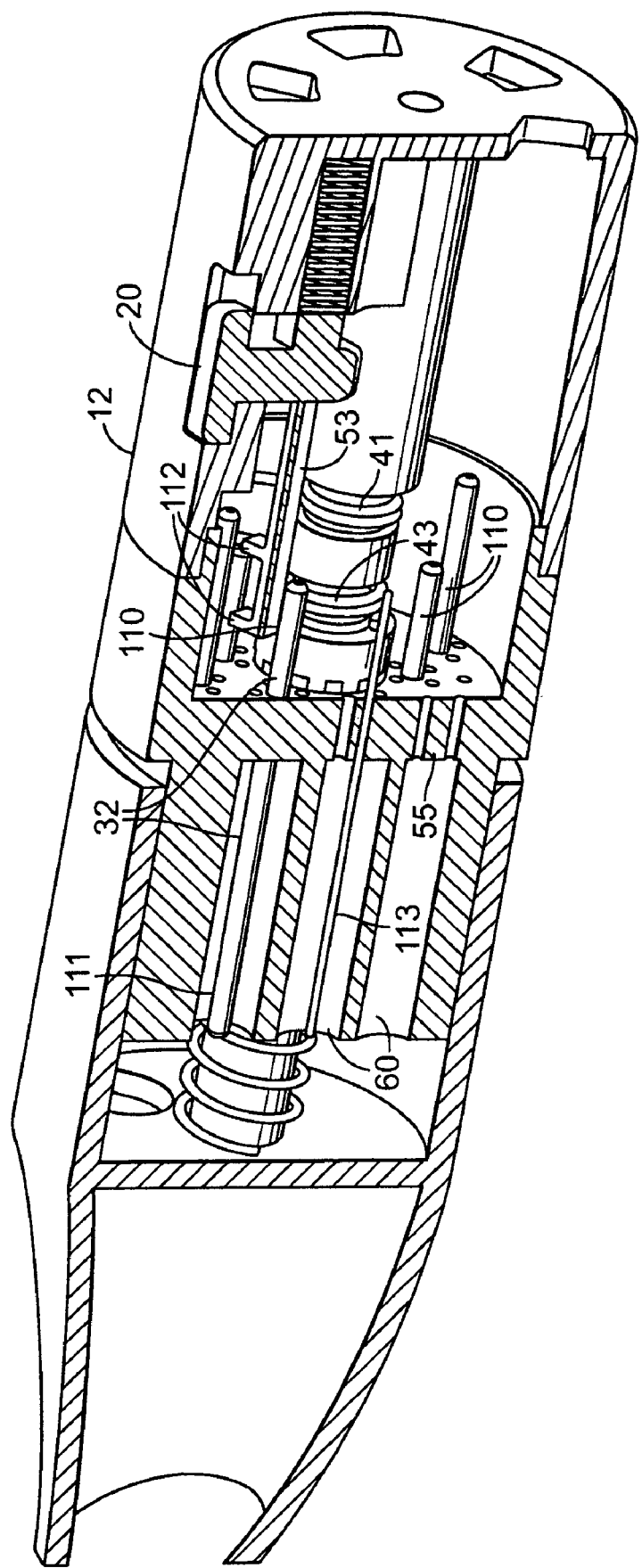
Figure 5:
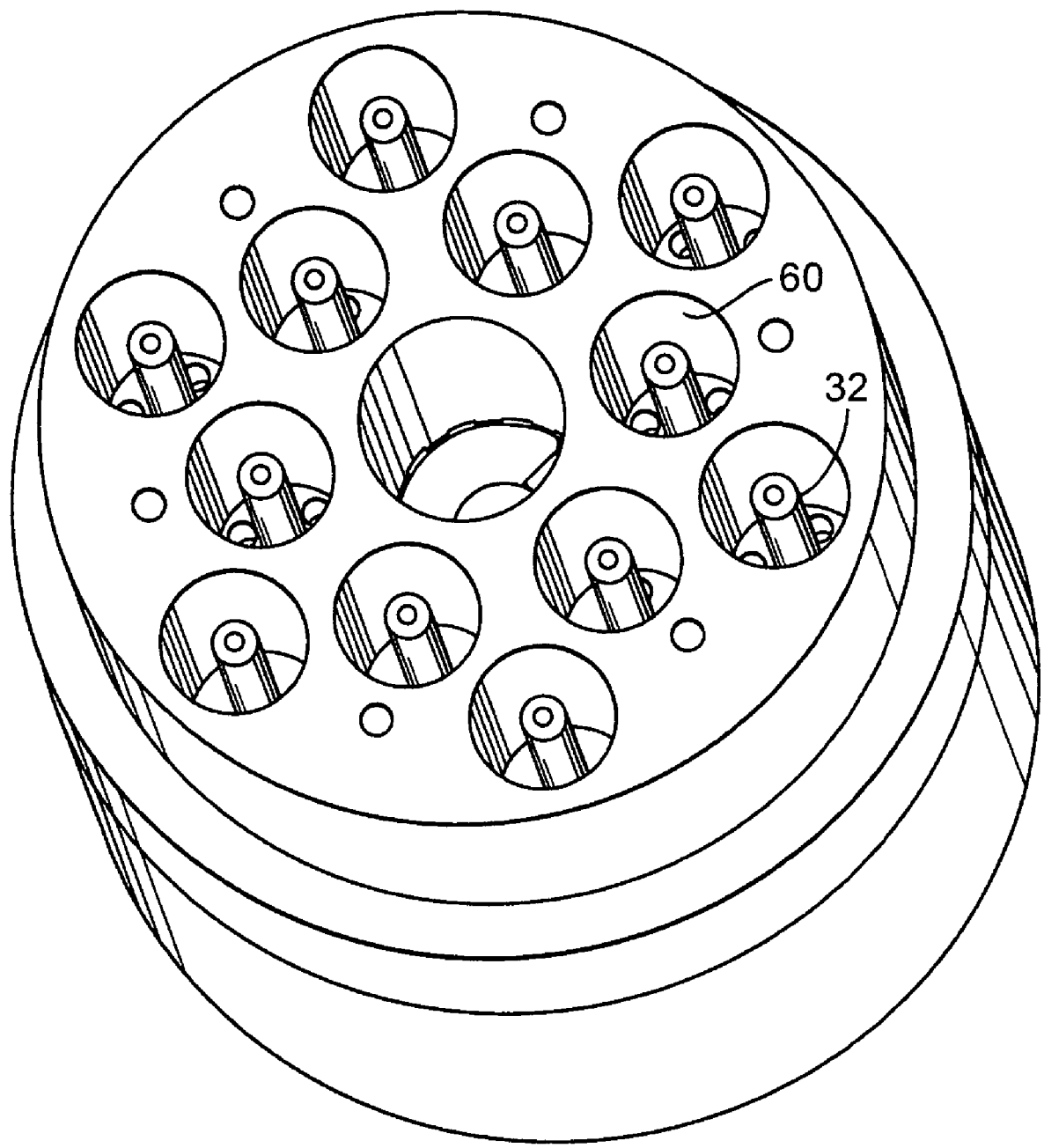

In FIG. 2, heat packages 32 are shown in an open configuration, meaning that there is not a feature separating each heat package 32 from adjacent heat packages. FIG. 4 shows another embodiment of a multi-dose drug delivery device incorporating a plurality of heat packages. In FIG. 4, heat packages 32 are formed from a sealed, cylindrical enclosure. One end of each heat package 32 comprises a percussive igniter 110, and the opposing end comprises a heating element 111. Each heat package 32 is retained by mounting plate 55. Heating element 111 of each heat package 32 is disposed within cylindrical recess 60. FIG. 5 show more clearly the heat package 32 disposed within the cylindrical recess 50. Recesses 60 can prevent drug vaporized from a heat package 32 from depositing on an adjacent heat package. Preventing deposition of vaporized drug on adjacent heat packages can be useful for maintaining a consistent amount of drug aerosol generated for each actuation of the device, and/or can facilitate producing high purity aerosols.

FIG. 4 also more clearly shows the structure of engagement arm 53 as comprising two members 112 perpendicular to the axis of engagement arm 53 and which are used to pull or push a striker arm (now shown) of torsion springs 41, and 43, from percussive igniter end 110 of heat package 32. Pulling or pushing a striker arm from percussive igniter end 110 frees the striker arm to impact a subsequent, non-activated heat package 32. FIG. 4 also shows a rod 113 disposed in a recess 60 and extending into the interior of endpiece 12. Rod 113 acts as a mechanical stop that holds the striker arm in a pre-stressed position prior to the first use of the device. For example, when a user first uses the device shown in FIG. 4, a striker arm can be resting on rod 113 in a pre-stressed condition. During the first use, the user pushes out on push-out switch 20, causing engagement arm 53 to pull or push a striker arm off rod 113, causing the striker arm to impact percussive igniter 110 of first heat package 32. First heat package 32 now holds the striker arm in a pre-stressed condition. During the second use, the user pushes on push-out switch 20 causing engagement arm 53 to pull or push the striker arm off first heat package 32, causing the striker arm to impact percussive igniter 110 of a second heat package 32. The process can be repeated until all heat packages 32 are activated.

The devices shown in FIGS. 2 and 4 can be used to administer an aerosol of a substance, such as a drug, to a patient. Each heat package 32 can be coated with a thin film of the substance or drug. The patient inhales on mouthpiece 14 to generate an air flow through the device, and at the same time, actuates push-out switch 20 to cause heat package 32 to vaporize the substance or drug, which then condenses in the airflow to form an aerosol of the substance or drug, which is then inhaled by a patient.

In certain embodiments, the overall assembled length of the multi-dose drug delivery device can range from about 3 inches to 6 inches, in certain embodiments from about 4 inches to about 4.6 inches.

As shown in FIG. 2, endpiece 12 includes a base section 35 and a mounting section 37 which are fixedly connected to form a single unit. Base section 35 includes one or more air inlets 16, a revolver mechanism 38 configured to provide an impact force for activating the percussive igniters, and a manually actuated push-out switch 20. Air inlets 16 include one or more holes in one end of endpiece 12. Revolver mechanism 38 includes a shaft on which is mounted a first torsion spring 41 and a second torsion spring 43. Torsion springs 41, 43 are wound around revolver mechanism 38, with a first end 45 fixed to shaft 38 and with a second end or striker arm 47 extending toward and capable of impacting the percussive igniters of heat packages 32. Push-out switch 20 including manual slide 49, compression spring 51 and engagement arm 53 is also incorporated into endpiece 12. Spring 51 maintains slide 20 in a pushed-in or non-actuated position. In a non-actuated position, striker arm 47 rests against a heat package 32 or a rest pin (not shown). Pushing out on slide 20 causes engagement arm to pull striker arm 47 off a heat package 32 so that striker arm 47 is free to impact the percussive igniter of a subsequent heat package.

Mounting section 37 includes a mounting plate 55 having a plurality of heat package mounting holes 61, a plurality of air holes 63, and an access hole 65 through which revolver shaft 38 is inserted. Heat packages 32 are inserted in heat package mounting holes 61 and can be held in place with an interference fit, press fit, an adhesive composition, or other such method. Heat packages 32 can be positioned at intervals around revolver shaft 38. Air holes 63 can be located around each of the heat packages 32 such that a sufficient airflow can pass over each heat package to form a substance or drug vaporized from the surface of the heat package.

A first end 67 of revolver shaft 38 is fixedly attached to air inlet end of base section 35. To assemble device 10, mounting section 37 is placed onto base section 35 by inserting revolver shaft 38 through access hole 65. Mouthpiece 14 can then be inserted over mounting section 37 and locked in place.

Actuation mechanisms other than the mechanical mechanism using torsion springs and a push-out switch can be used to provide a mechanical impact to activate a percussive igniter. Such actuation mechanisms include mechanical mechanisms, electrical mechanisms and inhalation mechanisms. Examples of other mechanical mechanisms include, but are not limited to, releasing a compression spring to impact the percussive igniter, releasing or propelling a mass to impact the percussive igniter, moving a lever to release a pre-stressed spring, and rotating a section of the device to stress and release a spring to impact a percussive igniter. Regardless of the mechanism employed in a particular drug delivery device, the actuation mechanism will produce sufficient impact force to deform the outer wall of the percussive igniter, and cause the initiator composition to deflagrate.

In certain embodiments, a drug delivery device can be a single dose device comprising a single heat package. In certain embodiments, wherein a section comprising the one or more percussively ignited heat package, and a section comprising the actuation mechanism are separable by the user, when the one or more heat packages have been activated, a new section comprising unused heat packages with a drug coating can be inserted, and the section comprising the actuation mechanism reused. In certain embodiments, the one or more heat packages and actuation mechanisms can be provided as a single unit that is not designed to be separated by a user. In such embodiments, after the one or more doses have been activated, the entire device can be discarded. Thus, in certain embodiments, the drug delivery device comprising a percussively activated heat package will comprise parts and materials that are low-cost and disposable.

Figure 6A:
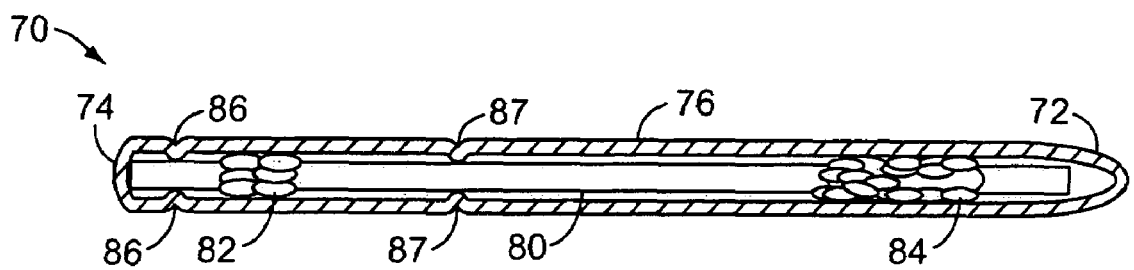
Figure 6B:
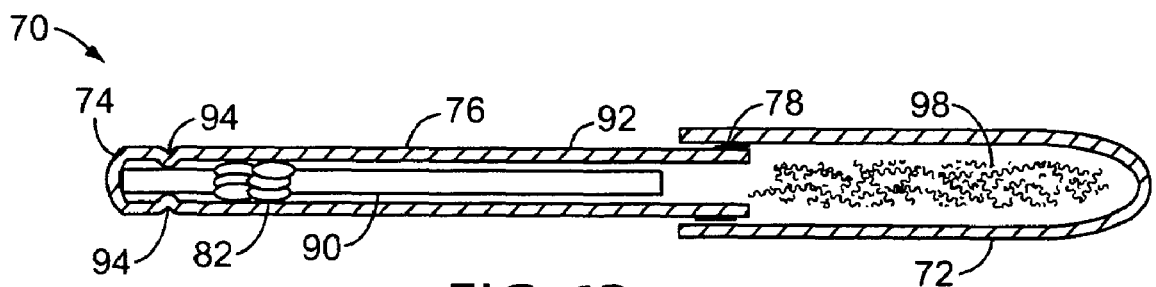

FIGS. 6A-6F show embodiments of heat packages comprising a percussive igniter. The heat packages 70 shown in FIGS. 6A-6F substantially comprise a sealed tube or cylinder 76 having a first end 72 and a second end 74. For use in a portable medical device, it is important that a heat package remain sealed when ignited and withstand any internal pressure generated by the burning fuels. In FIGS. 6A, and 6C-6F, first end 72 of heat package 70 is integral with the tubular body portion 76 or formed from the same part as tubular body portion 76. In FIG. 6B, first end 72 is a separate section and second end 74 is a separate section. Sections 72, 74 can be sealed at interface 78 by any appropriate means capable of withstanding the pressure and temperatures generated during combustion of the initiator and fuel compositions such as by soldering, welding, crimping, adhesively affixing, mechanically coupling, or the like. Second end 74 can also be sealed by similar means, and in certain embodiments, can include an insert, which may be thermally conductive or non-conductive.

FIG. 6A shows an embodiment of a heat package 70 having a coaxially positioned anvil 80 held in place by indentations 86, 87. Anvil 80 extends substantially the length of heat package 70. A thin coating of an initiator composition 82 is disposed toward one end of anvil 80, and a coating of a metal oxidation/reduction fuel composition 84 as disclosed herein is disposed on the other end of anvil 80. Indentations 87 provide space between anvil 80 and the inner wall of tube 70 to allow sparks produced during deflagration of initiator composition 82 to strike and ignite fuel composition 84. Anvil 80 can include features to facilitate retention of a greater amount of fuel and/or to facilitate assembly. For example, the end of anvil 80 on which fuel 84 is disposed can include fins or serrations to increase the surface area.

FIG. 6B shows an embodiment of a heat package 70 having an anvil 90 extending less than the length of heat package 70. Anvil 90 is held coaxially within tube 92 by indentations 94 toward one end of anvil 90. Minimizing or eliminating obstructions in the space between anvil 90 and the inner wall of tube 92 can facilitate the ability of sparks ejected from initiator composition 82 to strike and ignite fuel 98. First and second sections 72, 74 forming heat package 70 shown in FIG. 6B are sealed at interface 78. A fuel 98 is disposed within first section 72. Short anvil 90 permits the entire area within first section 72 to be filled with fuel 98.

Figure 6C:
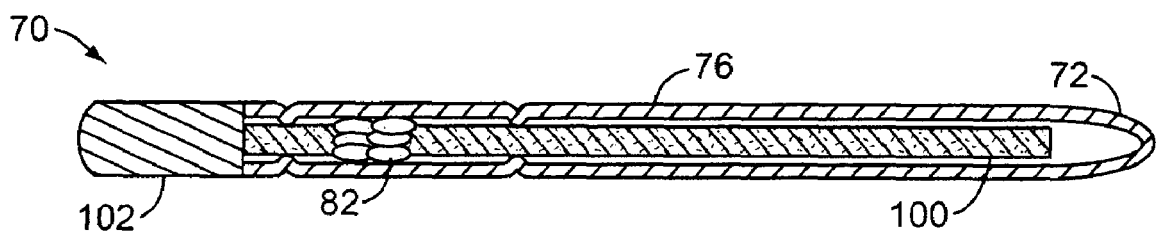

In FIG. 6C, anvil 100 comprises a fuel. Initiator composition 82 is disposed on part of the surface of anvil 100. Activation of initiator composition 82 can cause anvil 100 to ignite. End section 102 can be made of a thermally insulating material to facilitate mounting heat package 70. Use of a fuel extending substantially the length of the heat package can provide a larger usefully heated area.

Figure 6D:
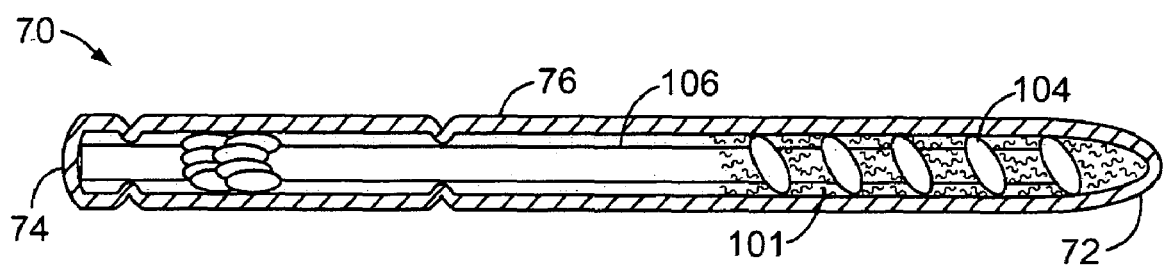

FIG. 6D shows an embodiment of heat package 70 in which the front end 104 of anvil 106 is formed with a high-pitch, thin-wall auger which can be used, for example, to load fuel 101 into cylinder end 72. Such a design can be useful in facilitating manufacturability of the heat package.

Figure 6E:
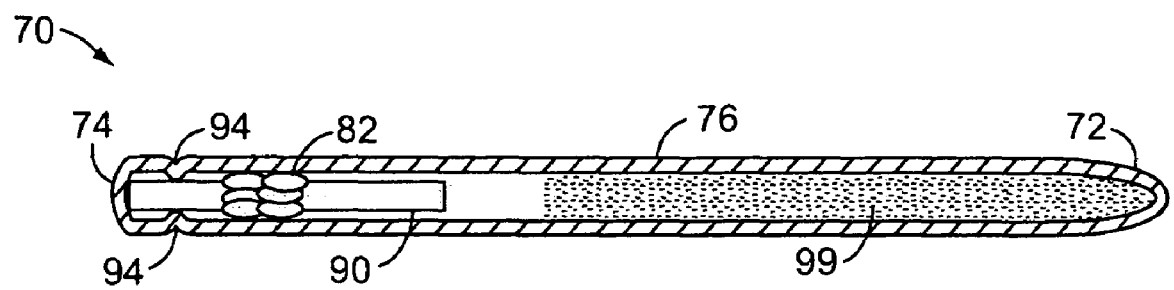
Figure 6F:
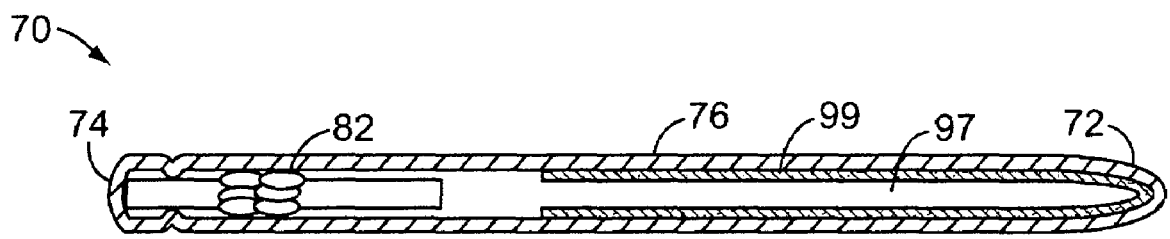

FIG. 6E shows an embodiment of heat package 70 in which anvil 90 extends part of the length of tube 76, and a substantial part of the interior of tube 76 is filled with a fuel 99. Anvil 90 is held in place by indentations 94. Initiator composition 82 is disposed on the anvil 90. Filing a substantial part of tube 76 with fuel 99 can increase the amount of heat generated by heat package 70. As shown in FIG. 6F, in certain embodiments, fuel 99 can be disposed as a layer on the inside wall of tube 76 and the center region 97 can be a space. A layer of fuel 99 can facilitate even heating of tube 76 and/or more rapidly reaching a maximum temperature by exposing a larger surface area that can be ignited by sparks ejected from initiator composition 82. A space in center region 97 can provide a volume in which released gases can accumulate to reduce the internal pressure of heat package 70.

FIG. 3, as discussed above, shows another embodiment of a heat package. Heat package 32 includes a first section 40 comprising a percussive igniter, and a second section 39 having a cross-sectional dimension greater than that of first section 40 comprising a fuel 50. The percussive igniter includes an anvil 44 coaxially disposed within a deformable tube 42. One end 45 of deformable tube 42 is sealed and the opposing end 57 is joined to section 39. Anvil 44 is held in place by indentations 46. A part of anvil 44 is coated with an initiator composition 48. Second section 39 comprises an enclosure having a wall thickness and cross-sectional dimension greater than that of first section 40. Such a design may be useful to increase the amount of fuel, to increase the external surface area on which a substance can be disposed, to provide a volume in which gases can expand to thereby reduce the pressure within the enclosure, to provide a greater fuel surface area for increasing the burn rate, and/or to increase the structural integrity of first section 40. In FIG. 3, fuel 50 is shown as a thin layer disposed along the inner wall of second section 39. Other fuel configurations are possible. For example, the fuel can be disposed only along the horizontal walls, can completely or partially fill internal area 52, and/or be disposed within fibrous matrix disposed throughout area 52. It will be appreciated that the shape, structure, and composition of fuel 50 can be determined as appropriate for a particular application that, in part, can be determined by the thermal profile desired. Heat package 32 further includes a thin film of substance 56 disposed on the outer surface of second section 39.

A heat package, such as shown in FIG. 3, and FIGS. 6A-6F, can have any appropriate dimension which can at least in part be determined by the surface area intended to be heated and the maximum desired temperature. Percussively activated heat packages can be particularly useful as compact heating elements capable of generating brief heat impulses such as can be used to vaporize a drug to produce a condensation aerosol for inhalation. In such applications, the length of a heat package can range from 0.4 inches to 2 inches and have a diameter ranging from 0.05 inches to 0.2 inches. In certain embodiments the anvil can be coiled in which case the length of the anvil can vary to based on the tightness of the coil and length required to ignite the fuel. The optimal dimensions of the anvil, the dimensions of the enclosed cylinder, and the amount of fuel disposed therein for a particular application and/or use can be determined by standard optimization procedures.

The self-contained heat packages can be percussively ignited by mechanically impacting the enclosure with sufficient force to cause the part of the enclosure to be directed toward the anvil, wherein the initiator composition is compressed between the tube and the anvil. The compressive force initiates deflagration of the initiator composition. Sparks produced by the deflagration are directed toward and impact the fuel composition, causing the fuel composition to ignite in a self-sustaining metal oxidation reaction generating a rapid, intense heat impulse.

Percussively activated initiator compositions are well known in the art. Initiator compositions for use in a percussive ignition system will deflagrate when impacted to produce intense sparking that can readily and reliably ignite a fuel such as a metal oxidation-reduction fuel. For use in enclosed systems, such as for example, for use in heat packages, it can be useful that the initiator compositions not ignite explosively, and not produce excessive amounts of gas. Certain initiator compositions are disclosed in U.S. patent application Ser. No. 10/851,018 entitled "Stable Initiator Compositions and Igniters," filed May 20, 2004, the entirety of which is incorporated herein by reference. Initiator compositions comprise at least one metal reducing agent, at least one oxidizing agent, and optionally at least one inert binder.

In certain embodiments, a metal reducing agent can include, but is not limited to molybdenum, magnesium, phosphorous, calcium, strontium, barium, boron, titanium, zirconium, vanadium, niobium, tantalum, chromium, tungsten, manganese, iron, cobalt, nickel, copper, zinc, cadmium, tin, antimony, bismuth, aluminum, and silicon. In certain embodiments, a metal reducing agent can include aluminum, zirconium, and titanium. In certain embodiments, a metal reducing agent can comprise more than one metal reducing agent.

In certain embodiments, an oxidizing agent can comprise oxygen, an oxygen based gas, and/or a solid oxidizing agent. In certain embodiments, an oxidizing agent can comprise a metal-containing oxidizing agent. Examples of metal-containing oxidizing agents include, but are not limited to, perchlorates and transition metal oxides. Perchlorates can include perchlorates of alkali metals or alkaline earth metals, such as but not limited to, potassium perchlorate ($KClO_4$), potassium chlorate ($KClO_3$), lithium perchlorate ($LiClO_4$), sodium perchlorate ($NaClO_4$), and magnesium perchlorate ($Mg(ClO_4)_2$). In certain embodiments, transition metal oxides that function as metal-containing oxidizing agents include, but are not limited to, oxides of molybdenum, such as $MoO_3$; oxides of iron, such as $Fe_2O_3$; oxides of vanadium, such as $V_2O_5$; oxides of chromium, such as $CrO_3$ and $Cr_2O_3$; oxides of manganese, such as $MnO_2$; oxides of cobalt such as $Co_3O_4$; oxides of silver such as $Ag_2O$; oxides of copper, such as $CuO$; oxides of tungsten, such as $WO_3$; oxides of magnesium, such as $MgO$; and oxides of niobium, such as $Nb_2O_5$. In certain embodiments, the metal-containing oxidizing agent can include more than one metal-containing oxidizing agent.

In certain embodiments, a metal reducing agent and a metal-containing oxidizing agent can be in the form of a powder. The term "powder" refers to powders, particles, prills, flakes, and any other particulate that exhibits an appropriate size and/or surface area to sustain self-propagating ignition. For example, in certain embodiments, the powder can comprise particles exhibiting an average diameter ranging from 0.01 μm to 200 μm.

In certain embodiments, the amount of oxidizing agent in the initiator composition can be related to the molar amount of the oxidizer at or near the eutectic point for the fuel compositions. In certain embodiments, the oxidizing agent can be the major component and in others the metal reducing agent can be the major component. Also, as known in the art, the particle size of the metal and the metal-containing oxidizer can be varied to determine the burn rate, with smaller particle sizes selected for a faster burn (see, for example, PCT WO 2004/011396). Thus, in some embodiments where faster burn is desired, particles having nanometer scale diameters can be used.

In certain embodiments, the amount of metal reducing agent can range from 25% by weight to 75% by weight of the total dry weight of the initiator composition. In certain embodiments, the amount of metal-containing oxidizing agent can range from 25% by weight to 75% by weight of the total dry weight of the initiator composition.

In certain embodiments, an initiator composition can comprise at least one metal, such as those described herein, and at least one metal-containing oxidizing agent, such as, for example, a chlorate or perchlorate of an alkali metal or an alkaline earth metal, or metal oxide, and others disclosed herein.

In certain embodiments, an initiator composition can comprise at least one metal reducing agent selected from aluminum, zirconium, and boron. In certain embodiments, the initiator composition can comprise at least one oxidizing agent selected from molybdenum trioxide, copper oxide, tungsten trioxide, potassium chlorate, and potassium perchlorate.

In certain embodiments, aluminum can be used as a metal reducing agent. Aluminum can be obtained in various sizes such as nanoparticles, and can form a protective oxide layer and therefore can be commercially obtained in a dry state.

In certain embodiments, the initiator composition can include more than one metal reducing agent. In such compositions, at least one of the reducing agents can be boron. Examples of initiator compositions comprising boron are disclosed in U.S. Pat. Nos. 4,484,960, and 5,672,843. Boron can enhance the speed at which ignition occurs and thereby can increase the amount of heat produced by an initiator composition.

In certain embodiments, reliable, reproducible and controlled ignition of a fuel can be facilitated by the use of an initiator composition comprising a mixture of a metal containing oxidizing agent, at least one metal reducing agent and at least one binder and/or additive material such as a gelling agent and/or binder. The initiator composition can comprise the same or similar reactants at as those comprising a metal oxidation/reduction fuel, as disclosed herein.

In certain embodiments, an initiator composition can comprise one or more additive materials to facilitate, for example, processing, enhance the mechanical integrity and/or determine the burn and spark generating characteristics. An inert additive material will not react or will react to a minimal extent during ignition and burning of the initiator composition. This can be advantageous when the initiator composition is used in an enclosed system where minimizing pressure is useful. The additive materials can be inorganic materials and can function, for example, as binders, adhesives, gelling agents, thixotropic, and/or surfactants. Examples of gelling agents include, but are not limited to, clays such as Laponite, Montmorillonite, Cloisite, metal alkoxides such as those represented by the formula R—Si(OR)$_n$ and M(OR)$_n$ where n can be 3 or 4, and M can be titanium, zirconium, aluminum, boron or other metal, and colloidal particles based on transition metal hydroxides or oxides. Examples of binding agents include, but are not limited to, soluble silicates such as sodium-silicates, potassium-silicates, aluminum silicates, metal alkoxides, inorganic polyanions, inorganic polycations, inorganic sol-gel materials such as alumina or silica-based sols. Other useful additive materials include glass beads, diatomaceous earth, nitrocellulose, polyvinylalcohol, guar gum, ethyl cellulose, cellulose acetate, polyvinylpyrrolidone, fluoro-carbon rubber (Viton) and other polymers that can function as a binder. In certain embodiments, the initiator composition can comprise more than one additive material.

In certain embodiments, additive materials can be useful in determining certain processing, ignition, and/or burn characteristics of an initiator composition. In certain embodiments, the particle size of the components of the initiator can be selected to tailor the ignition and burn rate characteristics as is known in the art, for example, as disclosed in U.S. Pat. No. 5,739,460.

In certain embodiments, it can be useful that the one or more additives be inert. When sealed within an enclosure, the exothermic oxidation-reduction reaction of the initiator composition can generate an increase in pressure depending on the components selected. In certain applications, such as in portable medical devices, it can be useful to contain the pyrothermic materials and products of the exothermic reaction and other chemical reactions resulting from the high temperatures generated within the enclosure.

In certain embodiments particularly appropriate for use in medical applications, it is desirable that the additive not be an explosive, as classified by the U.S. Department of Transportation, such as, for example, nitrocellulose. In certain embodiments, the additives can be Viton, Laponite or glass filter. These materials bind to the components of an initiator composition and can provide mechanical stability to the initiator composition.

The components of an initiator composition comprising the metal reducing agent, metal-containing oxidizing agent and/or additive materials and/or any appropriate aqueous- or organic-soluble binder, can be mixed by any appropriate physical or mechanical method to achieve a useful level of dispersion and/or homogeneity. For ease of handling, use and/or application, initiator compositions can be prepared as liquid suspensions or slurries in an organic or aqueous solvent.

The ratio of metal reducing agent to metal-containing oxidizing agent can be selected to determine the appropriate burn and spark generating characteristics. In certain embodiments, an initiator composition can be formulated to maximize the production of sparks having sufficient energy to ignite a fuel. Sparks ejected from an initiator composition can impinge upon the surface of a fuel, such as an oxidation/reduction fuel, causing the fuel to ignite in a self-sustaining exothermic oxidation-reduction reaction. In certain embodiments, the total amount of energy released by an initiator composition can range from 0.25 J to 8.5 J. In certain embodiments, a 20 μm to 100 μm thick solid film of an initiator composition can burn with a deflagration time ranging from 5 milliseconds to 30 milliseconds. In certain embodiments, a 40 μm to 100 μm thick solid film of an initiator composition can burn with a deflagration time ranging from 5 milliseconds to 20 milliseconds. In certain embodiments, a 40 μm to 80 μm thick solid film of an initiator composition can burn with a deflagration time ranging from 5 milliseconds to 10 milliseconds.

Examples of initiator compositions include compositions comprising 10% Zr, 22.5% B, 67.5% KClO$_3$; 49% Zr, 49% MoO$_3$, and 2% nitrocellulose; 33.9% Al, 55.4% MoO$_3$, 8.9% B, and 1.8% nitrocellulose; 26.5% Al, 51.5% MoO$_3$, 7.8% B, and 14.2% Viton; 47.6% Zr, 47.6% MoO$_3$, and 4.8% Laponite, where all percents are in weight percent of the total weight of the composition.

Examples of high-sparking and low gas producing initiator compositions comprise a mixture of aluminum, molybdenum trioxide, boron, and Viton. In certain embodiments, these components can be combined in a mixture of 20-30% aluminum, 40-55% molybdenum trioxide, 6-15% boron, and 5-20% Viton, where all percents are in weight percent of the total weight of the composition. In certain embodiments, an initiator composition comprises 26-27% aluminum, 51-52% molybdenum trioxide, 7-8% boron, and 14-15% Viton, where all percents are in weight percent of the total weight of the composition. In certain embodiments, the aluminum, boron, and molybdenum trioxide are in the form of nanoscale particles. In certain embodiments, the Viton is Viton A500.

In certain embodiments, the percussively activated initiator compositions can include compositions comprising a powdered metal-containing oxidizing agent and a powdered reducing agent comprising a central metal core, a metal oxide layer surrounding the core and a flurooalkysilane surface layer as disclosed, for example, in U.S. Pat. No. 6,666,936.

Typically, an initiator composition is prepared as a liquid suspension in an organic or aqueous solvent for coating the anvil and soluble binders are generally included to provide adhesion of the coating to the anvil.

A coating of an initiator composition can be applied to an anvil in various known ways. For example, an anvil can be dipped into a slurry of the initiator composition followed by drying in air or heat to remove the liquid and produce a solid adhered coating having the desired characteristic previously described. In certain embodiments, the slurry can be sprayed or spin coated on the anvil and thereafter processed to provide a solid coating. The thickness of the coating of the initiator composition on the anvil should be such, that when the anvil is placed in the enclosure, the initiator composition is a slight distance of around a few thousandths of an inch, for example, 0.004 inches, from the inside wall of the enclosure.

The fuel can comprise a metal reducing agent an oxidizing agent, such as, for example, a metal-containing oxidizing agent. In certain embodiments, the fuel can comprise a mixture of Zr and $MoO_3$, Zr and $Fe2O_3$, Al and $MoO_3$, or Al and $Fe_2O_3$. In certain embodiments, the amount of metal reduction agent can range form 60% by with to 90% by weight, and the amount of metal containing oxidizing agent can range from 40% by weight to 10% by weight.

Examples of useful metal reducing agents for forming a fuel include, but are not limited to, molybdenum, magnesium, calcium, strontium, barium, boron, titanium, zirconium, vanadium, niobium, tantalum, chromium, tungsten, manganese, iron, cobalt, nickel, copper, zinc, cadmium, tin, antimony, bismuth, aluminum, and silicon. In certain embodiments, a metal reducing agent can be selected from aluminum, zirconium, and titanium. In certain embodiments, a metal reducing agent can comprise more than one metal reducing agent.

In certain embodiments, an oxidizing agent for forming a fuel can comprise oxygen, an oxygen based gas, and/or a solid oxidizing agent. In certain embodiments, an oxidizing agent can comprise a metal-containing oxidizing agent. In certain embodiments, a metal-containing oxidizing agent includes, but is not limited to, perchlorates and transition metal oxides. Perchlorates can include perchlorates of alkali metals or alkaline earth metals, such as but not limited to, potassium perchlorate ($KClO_4$), potassium chlorate ($KClO_3$), lithium perchlorate ($LiClO_4$), sodium perchlorate ($NaClO_4$), and magnesium perchlorate ($Mg(ClO_4)_2$). In certain embodiments, transition metal oxides that function as oxidizing agents include, but are not limited to, oxides of molybdenum, such as $MoO_3$; iron, such as $Fe_2O_3$; vanadium, such as $V_2O_5$; chromium, such as $CrO_3$ and $Cr_2O_3$; manganese, such as $MnO_2$; cobalt such as $Co_3O_4$; silver such as $Ag_2O$; copper, such as CuO; tungsten, such as $WO_3$; magnesium, such as MgO; and niobium, such as $Nb_2O_5$. In certain embodiments, the metal-containing oxidizing agent can include more than one metal-containing oxidizing agent.

In certain embodiments, the metal reducing agent forming the solid fuel can be selected from zirconium and aluminum, and the metal-containing oxidizing agent can be selected from $MoO_3$ and $Fe_2O_3$.

The ratio of metal reducing agent to metal-containing oxidizing agent can be selected to determine the ignition temperature and the burn characteristics of the solid fuel. An exemplary chemical fuel can comprise 75% zirconium and 25% $MoO_3$, percentage by weight. In certain embodiments, the amount of metal reducing agent can range from 60% by weight to 90% by weight of the total dry weight of the solid fuel. In certain embodiments, the amount of metal-containing oxidizing agent can range from 10% by weight to 40% by weight of the total dry weight of the solid fuel.

In certain embodiments, a fuel can comprise one or more additive materials to facilitate, for example, processing and/or to determine the thermal and temporal characteristics of a heating unit during and following ignition of the fuel. An additive material can be inorganic materials and can function as binders, adhesives, gelling agents, thixotropic, and/or surfactants. Examples of gelling agents include, but are not limited to, clays such as Laponite, Montmorillonite, Cloisite, metal alkoxides such as those represented by the formula R—Si(OR)$_n$ and M(OR)$_n$ where n can be 3 or 4, and M can be titanium, zirconium, aluminum, boron or other metal, and colloidal particles based on transition metal hydroxides or oxides. Examples of binding agents include, but are not limited to, soluble silicates such as sodium-silicates, potassium-silicates, aluminum silicates, metal alkoxides, inorganic polyanions, inorganic polycations, inorganic sol-gel materials such as alumina or silica-based sols. Other useful additive materials include glass beads, diatomaceous earth, nitrocellulose, polyvinylalcohol, guar gum, ethyl cellulose, cellulose acetate, polyvinylpyrrolidone, fluoro-carbon rubber (VITON) and other polymers that can function as a binder.

Other useful additive materials include glass beads, diatomaceous earth, nitrocellulose, polyvinylalcohol, and other polymers that may function as binders. In certain embodiments, the fuel can comprise more than one additive material. The components of the fuel comprising the metal, oxidizing agent and/or additive material and/or any appropriate aqueous- or organic-soluble binder, can be mixed by any appropriate physical or mechanical method to achieve a useful level of dispersion and/or homogeneity. In certain embodiments, the fuel can be degassed.

The fuel in the heating unit can be any appropriate shape and have any appropriate dimensions. The fuel can be prepared as a solid form, such as a cylinder, pellet or a tube, which can be inserted into the heat package. The fuel can be deposited into the heat package as a slurry or suspension which is subsequently dried to remove the solvent. The fuel slurry or suspension can be spun while being dried to deposit the fuel on the inner surface of the heat package. In certain embodiments, the fuel can be coated on a support, such as the anvil by an appropriate method, including, for example, those disclosed herein for coating an initiator composition on an anvil.

In certain embodiments the anvil can be formed from a combustible metal alloy or metal/metal oxide composition, such as are known in the art, for example, PYROFUZE. Examples of fuel compositions suitable for forming the anvil are disclosed in U.S. Pat. Nos. 3,503,814; 3,377,955; and PCT Application No. WO 93/14044, the pertinent parts of each of which are incorporated herein by reference.

In certain embodiments, the fuel can be supported by a malleable fibrous matrix which can be packed into the heat package. The fuel comprising a metal reducing agent and a metal-containing oxidizing agent can be mixed with a fibrous material to form a malleable fibrous fuel matrix. A fibrous fuel matrix is a convenient fuel form that can facilitate manufacturing and provides faster burn rates. A fibrous fuel matrix is a paper-like composition comprising a metal oxidizer and a metal-containing reducing agent in powder form supported by an inorganic fiber matrix. The inorganic fiber matrix can be formed from inorganic fibers, such as ceramic fibers and/or glass fibers. To form a fibrous fuel, the metal reducing agent, metal-containing oxidizing agent, and inorganic fibrous material are mixed together in a solvent, and formed into a shape or sheet using, for example, paper-making equipment, and dried. The fibrous fuel can be formed into mats or other shapes as can facilitate manufacturing and/or burning.

In certain embodiments, a substance can be disposed on the outer surface of the percussively activated heat package. When activated, the heat generated by burning of the fuel can provide a rapid, intense thermal impulse capable of vaporizing a thin film of substance disposed on an exterior surface of the heat package with minimal degradation. A thin film of a substance can be applied to the exterior of a heat package by any appropriate method and can depend in part on the physical properties of the substance and the final thickness of the layer to be applied. In certain embodiments, methods of applying a substance to a heat package include, but are not limited to, brushing, dip coating, spray coating, screen printing, roller coating, inkjet printing, vapor-phase deposition, spin coating, and the like. In certain embodiments, the substance can be prepared as a solution comprising at least one solvent and applied to an exterior surface of a heat package. In certain embodiments, a solvent can comprise a volatile solvent such as acetone, or isopropanol. In certain embodiments, the substance can be applied to a heat package as a melt. In certain embodiments, a substance can be applied to a film having a release coating and transferred to a heat package. For substances that are liquid at room temperature, thickening agents can be admixed with the substance to produce a viscous composition comprising the substance that can be applied to a support by any appropriate method, including those described herein. In certain embodiments, a layer of substance can be formed during a single application or can be formed during repeated applications to increase the final thickness of the layer.

In certain embodiments, a substance disposed on a heat package can comprise a therapeutically effective amount of at least one physiologically active compound or drug. A therapeutically effective amount refers to an amount sufficient to effect treatment when administered to a patient or user in need of treatment. Treating or treatment of any disease, condition, or disorder refers to arresting or ameliorating a disease, condition or disorder, reducing the risk of acquiring a disease, condition or disorder, reducing the development of a disease, condition or disorder or at least one of the clinical symptoms of the disease, condition or disorder, or reducing the risk of developing a disease, condition or disorder or at least one of the clinical symptoms of a disease or disorder. Treating or treatment also refers to inhibiting the disease, condition or disorder, either physically, e.g. stabilization of a discernible symptom, physiologically, e.g., stabilization of a physical parameter, or both, and inhibiting at least one physical parameter that may not be discernible to the patient. Further, treating or treatment refers to delaying the onset of the disease, condition or disorder or at least symptoms thereof in a patient which may be exposed to or predisposed to a disease, condition or disorder even though that patient does not yet experience or display symptoms of the disease, condition or disorder.

In certain embodiments, the amount of substance disposed on a support can be less than 100 micrograms, in certain embodiments, less than 250 micrograms, and in certain embodiments, less than 1,000 micrograms, and in other embodiments, less than 3,000 micrograms. In certain embodiments, the thickness of a thin film applied to a heat package can range from 0.01 µm to 20 µm, and in certain embodiments can range from 0.5 µm to 10 µm.

In certain embodiments, a substance can comprise a pharmaceutical compound. In certain embodiments, the substance can comprise a therapeutic compound or a non-therapeutic compound. A non-therapeutic compound refers to a compound that can be used for recreational, experimental, or pre-clinical purposes. Classes of drugs that can be used include, but are not limited to, anesthetics, anticonvulsants, antidepressants, antidiabetic agents, antidotes, antiemetics, antihistamines, anti-infective agents, antineoplastics, antiparkinsonian drugs, antirheumatic agents, antipsychotics, anxiolytics, appetite stimulants and suppressants, blood modifiers, cardiovascular agents, central nervous system stimulants, drugs for Alzheimer's disease management, drugs for cystic fibrosis management, diagnostics, dietary supplements, drugs for erectile dysfunction, gastrointestinal agents, hormones, drugs for the treatment of alcoholism, drugs for the treatment of addiction, immunosuppressives, mast cell stabilizers, migraine preparations, motion sickness products, drugs for multiple sclerosis management, muscle relaxants, nonsteroidal anti-inflammatories, opioids, other analgesics and stimulants, ophthalmic preparations, osteoporosis preparations, prostaglandins, respiratory agents, sedatives and hypnotics, skin and mucous membrane agents, smoking cessation aids, Tourette's syndrome agents, urinary tract agents, and vertigo agents.

While it will be recognized that extent and dynamics of thermal degradation can at least in part depend on a particular compound, in certain embodiments, thermal degradation can be minimized by rapidly heating the substance to a temperature sufficient to vaporize and/or sublime the active substance. In certain embodiments, the substrate can be heated to a temperature of at least 250° C. in less than 500 msec, in certain embodiments, to a temperature of at least 250° C. in less than 250 msec, and in certain embodiments, to a temperature of at least 250° C. in less than 100 msec.

In certain embodiments, rapid vaporization of a layer of substance can occur with minimal thermal decomposition of the substance, to produce a condensation aerosol exhibiting high purity of the substance. For example, in certain embodiments, less than 10% of the substance is decomposed during thermal vaporization, and in certain embodiments, less than 5% of the substance is decomposed during thermal vaporization.

Examples of drugs that can be vaporized from a heated surface to form a high purity aerosol include albuterol, alprazolam, apomorphine HCl, aripiprazole, atropine, azatadine, benztropine, bromazepam, brompheniramine, budesonide, bumetanide, buprenorphine, butorphanol, carbinoxamine, chlordiazepoxide, chlorpheniramine, ciclesonide, clemastine, clonidine, colchicine, cyproheptadine, diazepam, donepezil, eletriptan, estazolam, estradiol, fentanyl, flumazenil, flunisolide, flunitrazepam, fluphenazine, fluticasone propionate, frovatriptan, galanthamine, granisetron, hydromorphone, hyoscyamine, ibutilide, ketotifen, loperamide, melatonin, metaproterenol, methadone, midazolam, naratriptan, nicotine, oxybutynin, oxycodone, oxymorphone, pergolide, perphenazine, pindolol, pramipexole, prochlorperazine, rizatriptan, ropinirole, scopolamine, selegiline, tadalafil, terbutaline, testosterone, tetrahydrocannabinol, tolterodine, triamcinolone acetonide, triazolam, trifluoperazine, tropisetron, zaleplon, zolmitriptan, and zolpidem. These drugs can be vaporized from a thin film having a thickness ranging from 0.1 µm to 20 µm, and corresponding to a coated mass ranging from 0.2 mg to 40 mg, upon heating the thin film of drug to a temperature ranging from 250° C. to 550° C. within less than 100 msec, to produce aerosols having a drug purity greater than 90% and in many cases, greater than 99%.

Nicotine is a heterocyclic compound that exists in both a free base and a salt form having the following structure:

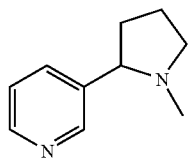

At 25° C., nicotine is a colorless to pale yellow volatile liquid. Nicotine has a melting point of −79° C., a boiling point at 247° C., and a vapor pressure of 0.0425 mmHg. The liquid nature prevents formation of stable films and the high vapor pressure can result in evaporation during shelf-life storage. While various approaches for preventing nicotine evaporation and degradation during shelf-life storage have been considered, for example, delivery from a reservoir via ink jet devices, chemical encapsulation of nicotine as a cyclodextrin complex, and nicotine containment in blister packs, such implementations have not been demonstrated to be amendable to low-cost manufacturing.

Figure 7:
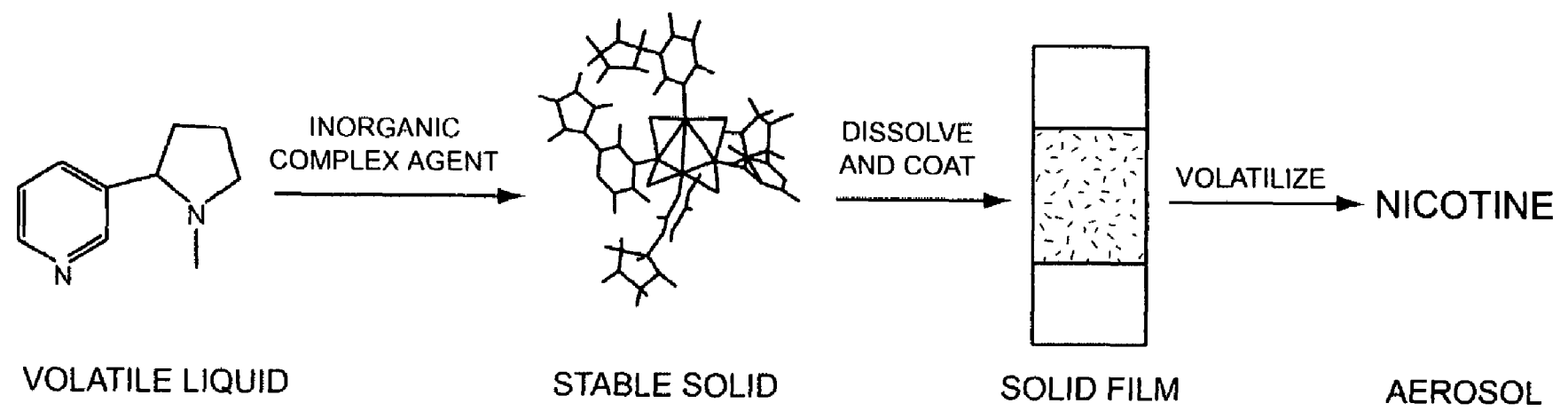

Volatile compounds, and in particular, nicotine, can be stabilized by forming a metal coordination complex, of the compound. FIG. 7 shows a conceptual summary of the use of inorganic metal complexes to stabilize a volatile compound. A volatile compound, such as nicotine, can form a complex with a metal or metal-containing complex to form a metal coordination complex of the compound. The metal coordination complex can include other ligands in addition to the volatile compound. The metal coordination complex comprising the volatile compound can be stable at standard temperature, pressure and environmental conditions. The metal coordination complex can be suspended or dissolved in a solvent, and the suspension or solution applied or deposited onto a substrate. After removing the solvent, a thin film of the metal coordination complex comprising the compound remains on the substrate. When complexed, the compound is stable such that the compound will not volatilize or degrade under standard conditions, and can be selectively volatilized when heated.

Appropriate metals and metal-containing compounds for forming thin films of volatile organic compounds are (i) capable of forming a stable composition at standard temperatures, pressures, and environmental conditions; (ii) capable of selectively releasing the volatile organic compound at a temperature that does not degrade, appreciably volatize, or react the metal-containing compound; (iii) capable of forming a complex with the volatile organic compound which is soluble in at least one organic solvent; and (iv) capable of releasing the volatile organic compound without appreciable degradation of the organic compound. In certain embodiments, the metal coordination complex comprises at least one metal salt. In certain embodiments, the at least one metal salt is selected from a salt of Zn, Cu, Fe, Co, Ni, Al, and mixtures thereof. In certain embodiment, the metal salt comprises zinc bromide ($ZnBr_2$).

Organic compounds particularly suited to forming metal coordination complexes include compounds comprising heterocyclic ring systems having one or more nitrogen and/or sulfur atoms, compounds having nitrogen groups, compounds having acid groups such as carboxyl and/or hydroxyl groups, and compounds having sulfur groups such as sulfonyl groups.

In certain embodiments, a stabilized, volatile organic compound such as a drug can be selectively volatilized from a metal coordination complex when heated to a temperature ranging from 100° C. to 600° C., and in certain embodiments can be selectively volatilized when heated to temperature ranging from 100° C. to 500° C., in other embodiments it can be selectively volatilized when heated to temperature ranging from 100° C. to 400° C. As used herein, "selectively vaporize" refers to the ability of the organic compound to be volatilized from the complex, while the metal and/or metal-containing compound is not volatilized, does not degrade to form volatile products, and/or does not react with the organic compound to form volatile reaction products comprising components derived from the metal-containing compound. Use of the term "selectively vaporize" includes the possibility than some metal-containing compound, degradation product, and/or reaction product may be volatilized at a temperature which "selectively vaporizes" the organic complex. However, the amount of metal-containing compound, degradation product, and/or reaction product will not be appreciable such that a high purity of organic compound aerosol is produced, and the amount of any metal-containing compound and/or derivative thereof is within FDA guidelines.

Formation of high yield, high purity aerosols comprising a compound such as a drug can be facilitated by rapidly vaporizing thin films. It is therefore desirable that the metal coordination complexes be capable of being applied or deposited on a substrate as thin films. Thin films can be applied or deposited from a solvent phase, a gas phase, or a combination thereof. In certain embodiments, thin films of a metal coordination complex can be applied from a suspension of solution of a solvent. The solvent can be a volatile solvent that can be removed from the deposited thin film, for example, under vacuum and temperature. A metal coordination complex suspended or dissolved in a solvent can be applied by any appropriate method such as spray coating, roller coating, dip coating, spin coating, and the like. A metal coordination complex can also be deposited on a substrate from the vapor phase.

Metal coordination complexes of zinc bromide ($ZnBr_2$) and nicotine were prepared and evaluated. $ZnBr_2$ is an off-white solid having a melting point of 394° C., a boiling point of 650° C., and a decomposition temperature of 697° C. $ZnBr_2$ is stable under normal temperatures and pressures. The $(nicotine)_2$-$ZnBr_2$ metal salt complex was prepared as disclosed herein. The $(nicotine)_2$-$ZnBr_2$ metal salt complex is a solid with a melting point of 155° C.

The nicotine aerosol yield was determined by measuring the amount of nicotine in the aerosol produced by vaporizing thin films of the $(nicotine)_2$-$ZnBr_2$ complex. Thin film coatings of $(nicotine)_2$-$ZnBr_2$ having a thickness of 2 μm or 6 μm were prepared as disclosed herein. The amount of nicotine comprising a 2 μm, and 6 μm thin film of $(nicotine)_2$-$ZnBr_2$ was about 1.17 mg and about 3.5 mg, respectively. The metal foil substrate on which a thin film of $(nicotine)_2$-$ZnBr_2$ was disposed, was positioned within an airflow of about 20 L/min. Films were heated to a maximum temperature of 300 C., 350° C., 400° C. or 500° C. within less than about 200 msec, by applying a current to the metal foil substrate. The aerosol produced during selective vaporization of the $(nicotine)_2$-$ZnBr_2$ film was collected on an oxalic acid coated filter, and the amount of collected nicotine determined by high pressure liquid chromatography. The percent nicotine yield in the aerosol was the amount of nicotine collected on the filter as determined by HPLC divided by the amount of nicotine in the thin film deposited on the metal foil substrate.

As shown in FIG. 8, the average yield of nicotine in the aerosol from a vaporized 2 μm thick thin film of $(nicotine)_2$-

ZnBr$_2$ was about 60±7% over a temperature range of 300° C. to 400° C. The average yield of nicotine in the aerosol obtained upon vaporizing a 6 μm thick thin film of (nicotine)$_2$-ZnBr$_2$ was about 51±2% when the metal foil was heated to a maximum temperature of 300° C., and increased to about 73±1 percent when the metal foil was heated to a maximum temperature of 400° C.

Figure 9:
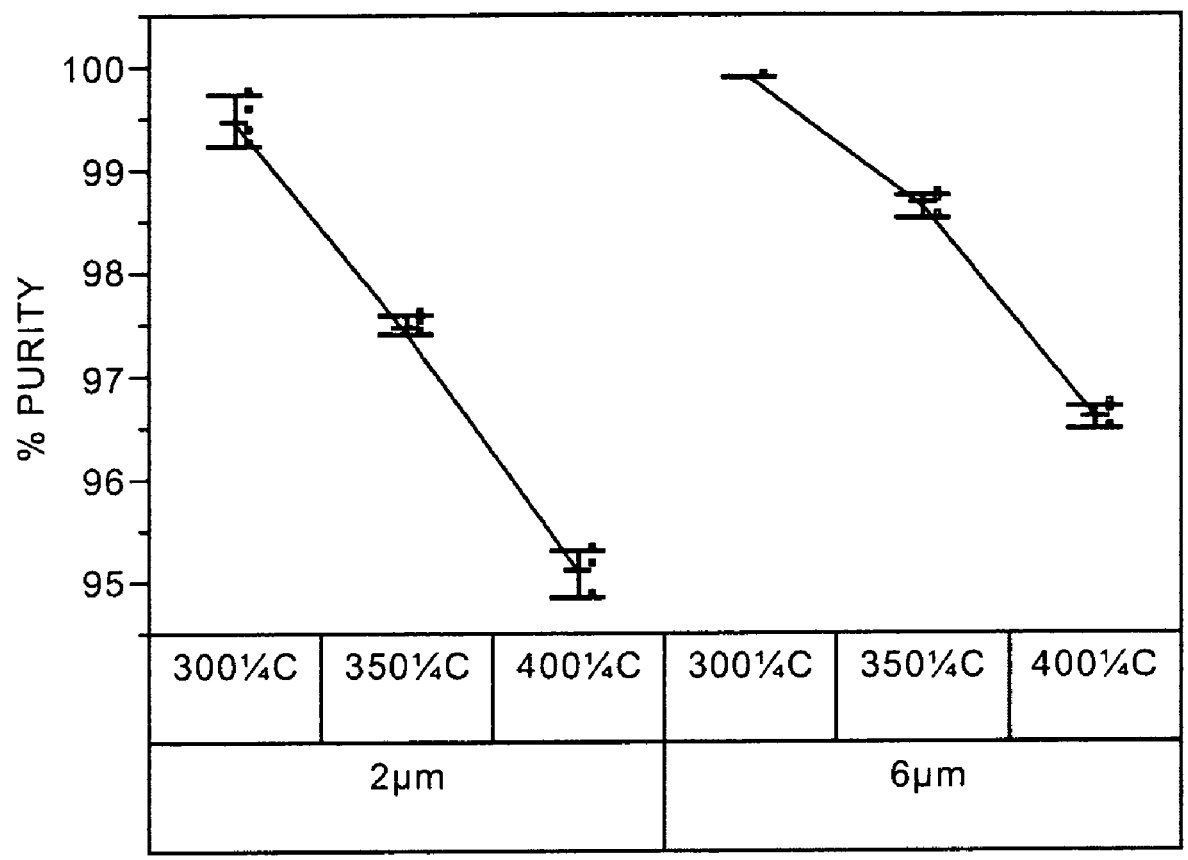

The purity of nicotine in an aerosol produced by vaporizing thin films of (nicotine)$_2$-ZnBr$_2$ was also determined. The percent purity of nicotine in the aerosol was determined by comparing the area under the curve representing nicotine with the area under the curve for all other components separated by HPLC. As shown in FIG. 9, the average nicotine purity of the aerosol obtained by vaporizing 2 μm and 6 μm thick thin films of (nicotine)$_2$-ZnBr$_2$ at a maximum temperature of 300° C. was about 99.5% and about 99.99%, respectively. The nicotine purity of the aerosol decreased when the thin film of (nicotine)$_2$-ZnBr$_2$ was heated to a maximum temperature of greater than 300° C. Also, for a given vaporization temperature, the purity of the nicotine aerosol derived from a 6 μm thick thin film of (nicotine)$_2$-ZnBr$_2$ was greater than the purity of the nicotine aerosol derived from a 2 μm thick solid film of (nicotine)$_2$-ZnBr$_2$.

While aerosols having a mean mass aerodynamic diameter ranging from 1 to 5 are predominately deposited in the lungs, aerosols of volatile compounds can vaporize during inhalation. The re-vaporized compounds can then be deposited in the mouth or throat resulting in irritation and/or unpleasant taste. The use of rapid vaporization to form a dense bolus of aerosol helps to minimize or prevent re-vaporization of an aerosol formed from a volatile compound. Additionally, re-vaporization can be minimized by the use of appropriate additives included in the metal coordination complex. For example, compounds such as propylene glycol, polyethylene glycol, and the like, can be used. To mask unpleasant flavors, compounds such as menthol, and the like, can be included in the complexes.

Metal coordination complexes can be used to stabilize volatile compounds such as nicotine for use in drug delivery devices as disclosed herein. A metal coordination complex comprising a drug can be applied as a thin film to the exterior surface of a percussively activated heat package. For example, a metal coordination complex comprising a drug can be applied to element 30 of FIG. 2 or element 111 of FIG. 4. Activation of a percussive igniter can ignite a fuel and heat the exterior surface of the heat package and the thin film of a metal coordination complex comprising the drug. The drug can then be selectively vaporized from the metal coordination complex. Thin films of metal coordination complexes comprising drugs and/or other volatile compounds can be used in other drug delivery devices. For example, in certain embodiments, thin films of metal coordination complexes can be used in drug delivery devices in which a resistively heat metal foil as disclosed in U.S. application Ser. No. 10/861,554 is used to heat a thin solid film disposed thereon. In certain embodiments, thin films of metal coordination complexes can be used in drug delivery devices in which an electrically resistive heating element is used to ignite a spark-generating initiator composition, which when activated, ignites a metal oxidation/reduction fuel as disclosed in U.S. application Ser. No. 10/850,895.

In certain embodiments, thin films of a metal coordination complex of a drug can be used to provide multiple doses of a drug provided on a spool or reel of tape. For example, a tape can comprise a plurality of drug supply units with each drug supply unit comprising a heat package on which a thin film comprising a metal coordination complex comprising a drug is disposed. Each heat package can include an initiator composition that can be ignited, for example, by resistive heating or percussively, and a fuel capable of providing a rapid, high temperature heat impulse sufficient to selectively vaporize the drug from the metal coordination complex. Each heat package can be spaced at intervals along the length of the tape. During use, one or more heat packages can be positioned within an airway and, while air is flowing through the airway, the heat package can be activated to selectively vaporize the drug from the metal coordination complex. The vaporized drug can condense in the air flow to form an aerosol comprising the drug which can then be inhaled by a user. The tape can comprise a plurality of thin films that define the regions where the initiator composition, fuel, and thin film comprising a drug are disposed. Certain of the multiple layers can further provide unfilled volume for released gases to accumulate to minimize pressure buildup. The plurality of layers can be formed from any material which can provide mechanical support and that will not appreciably chemically degrade at the temperatures reached by the heat package. In certain embodiments, a layer can comprise a metal or a polymer such as polyimide, fluoropolymer, polyetherimide, polyether ketone, polyether sulfone, polycarbonate, or other high temperature resistance polymers. In certain embodiments, the tape can further comprise an upper and lower layer configured to physically and/or environmentally protect the drug or metal coordination complex comprising a drug. The upper and/or lower protective layers can comprise, for example, a metal foil, a polymer, or can comprise a multilayer comprising metal foil and polymers. In certain embodiments, protective layers can exhibit low permeability to oxygen, moisture, and/or corrosive gases. All or portions of a protective layer can be removed prior to use to expose a drug and fuel. The initiator composition and fuel composition can comprise, for example, any of those disclosed herein. Thin film heat packages and drug supply units in the form of a tape, disk, or other substantially planar structure, can provide a compact and manufacturable method for providing a large number of doses of a substance. Providing a large number of doses at low cost can be particularly useful in certain therapies, such as for example, in administering nicotine for the treatment of nicotine craving and/or effecting cessation of smoking.

Figure 10:
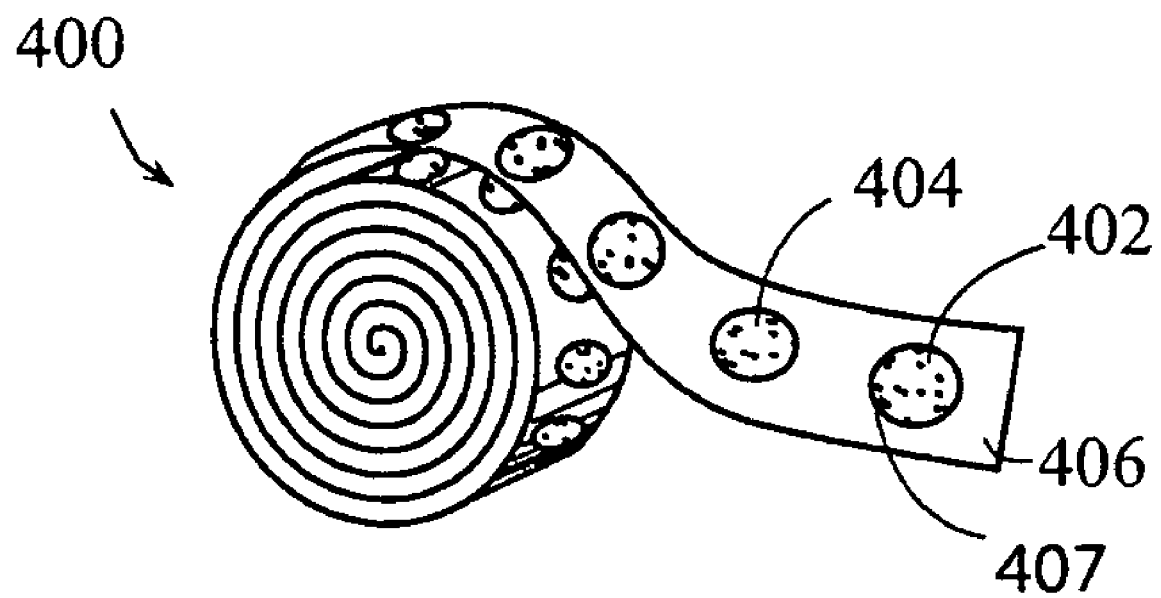

FIG. 10 illustrates a certain embodiment of a drug supply unit configured for use in a drug delivery device designed for multiple uses using a spool or reel of tape. As shown in FIG. 10, a tape 406 in the form of a spool or reel 400 comprises a plurality of drug supply units 402, 404. The plurality of drug supply units 402, 404 can comprise a heating unit on which is disposed a thin film of a drug or a drug/complex to be thermally vaporized. Covering the thin film is a fine mesh 407 e.g., metal wire, to hold or retain the drug and/or drug complex on the heating unit. The complex can have adhesion difficulties particularly at thick film thicknesses, the use of the mesh can help prevent flaking or dissociation of the drug complex from the surface of the tape or reel The mesh can be a layer the covers the length of the tape 406 or separate units of mesh to cover each area of drug film. Each of the plurality of drug supply units 402, 404 can comprise the same features as those described herein. In certain embodiments, tape 406 can comprise a plurality of heating units. Each heating unit can comprise a solid fuel and an initiator composition adjacent to the solid fuel, which upon striking of the initiator composition can cause the initiator composition to spark and ignite the fuel, resulting in vaporization of the drug. The tape can be advanced in a device using a reel mechanism (not shown) and a spring or other mechanism can be used to actuate the initiator composition by striking.

Drug aerosols formed by selective vaporization of a drug from a metal coordination complex can be used for the pulmonary administration of drugs and for the treatment of diseases and conditions. Accordingly, nicotine aerosols can be used to treat nicotine craving experienced by persons attempting to withdraw from nicotine use, and for effecting smoking cessation. Nicotine aerosols provided to the lungs of a user are expected to simulate the pharmacokinetic profile and blood nicotine concentrations obtained from smoking cigarettes. Therefore, it is anticipated that effective therapies directed to reducing nicotine craving and smoking cessation can be developed using nicotine aerosols generated by the devices and methods disclosed herein.

EXAMPLES

Embodiments of the present disclosure can be further defined by reference to the following examples, which describe in detail preparation of the compounds of the present disclosure. It will be apparent to those skilled in the art that many modifications, both to the materials and methods, may be practiced without departing from the scope of the present disclosure.

Example 1

Preparation of Solid Thin Films of Nicotine Metal Coordination Complexes

A solution of 2% oxalic acid was prepared by dissolving 20 g of oxalic acid in 1 L of acetone. Glass fiber filters (Whatman) were coated with oxalic acid by dipping the filters in the 2% oxalic acid solution for about 10 seconds. The oxalic acid coated filters were air dried.

A (nicotine)$_2$-ZnBr$_{2(s)}$ complex was prepared by first dissolving solid ZnBr$_2$ in ethanol to form a 1 M solution. A 2M nicotine solution was prepared by suspending nicotine in ethanol. The ZnBr$_2$ and nicotine solutions were combined and mixed. The resulting solid complex was repeatedly washed with methanol using vacuum filtration, and subsequently dried. The molar ration of nicotine to ZnBr$_2$ in the nicotine-ZnBr$_2$ complex was 2:1.

To coat metal foils, the (nicotine)$_2$-ZnBr$_2$ complex was dissolved in chloroform. The (nicotine)$_2$-ZnBr$_2$ complex was hand coated onto 0.005 inch thick stainless foils. The coatings were dried under vacuum for about 1 hour at 25° C. The coatings of (nicotine)$_2$-ZnBr$_2$ complex were stored in a vacuum and protected from light prior to use.

The coatings of (nicotine)$_2$-ZnBr$_2$ complex were vaporized by applying a current to the metal foil sufficient to heat the coatings to temperatures of 300° C., 350° C., and 400° C. The aerosol formed by vaporizing the coating in an air flow of 20 L/min was analyzed by collecting the aerosol on oxalic acid coated filters. The collected aerosol was extracted from the filters with 5 mL of an aqueous solution containing 0.1% TFA. The purities of the extracts were determined using high pressure liquid chromatography and are shown in FIG. 9. A Varian HPLC system having a single XTerra RP18, 4.6×150 mm column, with an eluant solution comprising a 75% aqueous phase of perchloric acid solution with one ampoule of 1-octanesulfonic acid sodium salt concentrate at pH 2, and a 25% organic phase of acetonitrile was used. The HPLC was performed under isocratic run conditions for 20 minutes.

Example 2

Determination of Particle Size of Nicotine Aerosol from Vaporization of Nicotine from a Nicotine ZnBr$_2$ Complex A solution of 2% oxalic acid was prepared by dissolving 20 g of oxalic acid (Aldrich) in 1 L of acetone (J T Baker). GF 50, Ø81 mm glass fiber filters (Schleicher & Schuell) were coated with oxalic acid by dipping the filters in the 2% oxalic acid solution for about 10 seconds. The oxalic acid coated filters were air dried overnight.

A (nicotine)$_2$-ZnBr$_{2(s)}$ complex was prepared by first dissolving solid ZnBr$_2$ in ethanol to form a 1 M solution. A 2M nicotine solution was prepared by suspending nicotine in ethanol. The ZnBr$_2$ and nicotine solutions were combined and mixed. The resulting solid complex was repeatedly washed with methanol using vacuum filtration, and subsequently dried. The molar ration of nicotine to ZnBr$_2$ in the nicotine-ZnBr$_2$ complex was 2:1.

To coat metal foils, the (nicotine)$_2$-ZnBr$_2$ complex was dissolved in chloroform. Two separate coating thickness of the (nicotine)$_2$-ZnBr$_2$ complex on stainless steel were prepared. A 169.4 mg/mL solution of (nicotine)$_2$-ZnBr$_2$ complex in chloroform and a 338.8 mg/mL solution of (nicotine)$_2$-ZnBr$_2$ complex in chloroform were made. Exposure to light was minimized at all times during and after formation of these solutions. The (nicotine)$_2$-ZnBr$_2$ complex for each solution was hand coated onto 0.005 inch thick stainless foils using a 10 uL Hamilton syringe. 5.9 uL of the 169.4 mg/mL (nicotine)$_2$-ZnBr$_2$ complex solution was coated onto both sides of an area of 1.27 cm×2.3 cm of stainless steel. This corresponds to a 2 μm film thickness coating which contained about 1 mg of nicotine. Similarly, 8.8 μL of the 338.8 mg/mL (nicotine)$_2$-ZnBr$_2$ complex solution was coated onto both sides of an area of 1.27 cm×2.3 cm of stainless steel. This corresponds to a 6 μm film thickness coating which contained about 3.5 mg of nicotine The coatings were dried under vacuum for about 1 hour at 25° C. The coatings of (nicotine)$_2$-ZnBr$_2$ complex were stored in a vacuum for at least 30 minutes and protected from light prior to use.

The coatings of (nicotine)$_2$-ZnBr$_2$ complex were vaporized by applying a current of 13.0V to the metal foil sufficient to heat the coatings to temperature of 350° C. The aerosol formed by vaporizing the coating in an air flow of 28.3 L/min was analyzed by collected the aerosol on oxalic acid coated filters using an 8 stage Anderson impactor. The MMAD of the nicotine aerosol from the 2 μm thick (nicotine)$_2$-ZnBr$_2$ complex was determined to be 2.00. Likewise, the MMAD of the nicotine aerosol from the 6 μm thick (nicotine)$_2$-ZnBr$_2$ complex was determined to be 1.79. After vaporization the filters were extracted with 5 mL of 0.1% trifluoroacetic acid/DI H$_2$O and analyzed by HPLC. The purity of the nicotine aerosol from the 2 μm thick (nicotine)$_2$-ZnBr$_2$ complex was determined to be greater than 97%. Whereas the purity of the nicotine aerosol from the 6 μm thick (nicotine)$_2$-ZnBr$_2$ complex was determined to be greater than 97%.

Example 3

Preparation of Initiator Composition for Percussive Heat Packages

An initiator composition was formed by combining 620 parts by weight of titanium having a particle size less than 20

μm, 100 parts by weight of potassium chlorate, 180 parts by weight red phosphorous, 100 parts by weight sodium chlorate, and 620 parts by weight water, and 2% polyvinyl alcohol binder.

Example 4

Percussively Ignited Heat Package

The ignition assembly comprising a ¼ inch section of a thin stainless steel wire anvil was dip coated with the initiator composition and dried at about 40-50 C. for about 1 hour. The dried, coated wire anvil was inserted into a 0.003 inch thick or 0.005 inch thick, soft walled aluminum tube that was about 1.65 inches long with an outer diameter of 0.058 inches. The tube was crimped to hold the wire anvil in place and sealed with epoxy.

In the other end of the aluminum tube was placed the fuel. In order to form a mat of heating powder fuel using glass fiber as the binder, 1.3 grams of glass fiber filter paper was taken and added to about 50 mL of water with rapid stirring. After the glass fiber had separated and become suspended in the water, 6 g of $MoO_3$ was added. This was followed with the addition of 3.8 g of Zr (3 μm). After stirring for 30 min, at room temperature the mixture was filtered on standard filter paper and the resulting mat dried at high vacuum at 60° C. A 0.070 inch thick mat was formed which rapidly burns. After manually packing the fuel in the end of the heat package that did not contain the anvil, the fuel end of the soft walled aluminum tube was sealed.

In other embodiments, the fuel was packed into a 0.39 inch length of aluminum sleeve having a 0.094 in outer diameter and inserted over a soft walled aluminum tube (0.003 inch thick or 0.0005 inch thick) that was about 1.18 inches long with an outer diameter of 0.058 that was sealed at one end and had a dried coated wire anvil inserted. The fuel coated aluminum sleeve was sealed until the soft walled aluminum tube by crimping.

The heat packages were coated with drug and percussively ignited using mechanical activation of a spring or breath actuation of a spring.

In some embodiments a fuel mixture comprising Laponite was used. The following procedure was used to prepare solid fuel coatings comprising 76.16% Zr: 19.04% $MoO_3$: 4.8% Laponite® RDS.

To prepare wet Zirconium (Zr), the as-obtained suspension of Zr in DI water (Chemetall, Germany) was agitated on a roto-mixer for 30 minutes. Ten to 40 mL of the wet Zr was dispensed into a 50 mL centrifuge tube and centrifuged (Sorvall 6200RT) for 30 minutes at 3,200 rpm. The DI water was removed to leave a wet Zr pellet.

To prepare a 15% Laponite® RDS solution, 85 grams of DI water was added to a beaker. While stirring, 15 grams of Laponite® RDS (Southern Clay Products, Gonzalez, Tex.) was added, and the suspension stirred for 30 minutes.

The reactant slurry was prepared by first removing the wet Zr pellet as previously prepared from the centrifuge tube and placed in a beaker. Upon weighing the wet Zr pellet, the weight of dry Zr was determined from the following equation: Dry Zr (g)=0.8234 (Wet Zr (g))−0.1059.

The amount of molybdenum trioxide to provide a 80:20 ratio of Zr to $MoO_3$ was then determined, e.g, $MoO_3$=Dry Zr (g)/4, and the appropriate amount of $MoO_3$ powder (Accumet, N.Y.) was added to the beaker containing the wet Zr to produce a wet Zr: $MoO_3$ slurry. The amount of Laponite®RDS to obtain a final weight percent ratio of dry components of 76.16% Zr: 19.04% $MoO_3$: 4.80% Laponite® RDS was determined. Excess water to obtain a reactant slurry comprising 40% DI water was added to the wet Zr and $MoO_3$ slurry. The reactant slurry was mixed for 5 minutes using an IKA Ultra-Turrax mixing motor with a S25N-8G dispersing head (setting 4). The amount of 15% Laponite® RDS previously determined was then added to the reactant slurry, and mixed for an additional 5 minutes using the IKA Ultra-Turrax mixer. The reactant slurry was transferred to a syringe and stored for at least 30 minutes prior to coating.

The Zr: $MoO_3$: Laponite® RDS reactant slurry was then deposited into the heat packages and allowed to dry.

Example 5

Generation of an Alprazolam Aerosol using Vaporization from a Percussively Ignited Heat Package On an assembled heat package was coated manually a solution of alprazolam in dichloromethane using a syringe to apply the coating solution to the end of the heat package containing the fuel (full length of heat package was 1.18 in., drug coated length of the heat package was about 0.39 in). Two to three microliters of solution containing the alprazolam were applied to coat 0.125 mg of alprazolam at a film thickness of 1.58 μm. The coated heat package was dried for at least 30 minutes inside a fume hood. The last traces of solvent were removed in vacuo for 30 minutes prior to vaporization experiments.

After mechanical actuation of the heat package, the aerosol formed by vaporizing the coating in an air flow of 20 L/min at a temperature of greater than 800° C. were collected by passing the air stream containing the aerosol through a PTFE membrane filter (25 mm diameter, 1 μm pore size, Pall Life Sciences) mounted in a Delrin filter (25 mm) holder (Pall Life Sciences). The filter was extracted with 1 ml of acetonitrile (HPLC grade). The filter extract was analyzed by high performance liquid chromatography (HPLC) using a C-18 reverse phase column (4.6 mm ID×150 mm length, 5 μm packing, "Capcell Pak UG120," Shiseido Fine Chemicals, Tokyo, Japan). For alprazolam, a binary mobile phase of eluant A (0.1% trifluoroacetic acid in water) and eluant B (0.1% trifluoroacetic acid in acetonitrile) was used with a 5-95% B linear gradient (24 min) at a flow rate of 1 mL/min. Detection was at 200-400 nm using a photodiode array detector. Purity was calculated by measuring peak areas from the chromatogram. The purity of the resultant aerosol was determined to be 96.8% with a recovered yield of 100%. To increase the purity of the aerosol, one can use lower temperatures for vaporization.

Example 6

Generation of a Pramipexole Aerosol using Vaporization from a Percussively Ignited Heat Package On an assembled heat package was coated manually a solution of pramipexole in methanol using a syringe to apply the coating solution to the end of the heat package containing the fuel (full length of heat package was 1.18 in., drug coated length of the heat package was about 0.39 in). Two to three microliters of solution containing the pramipexole were applied to coat 0.500 mg of pramipexole at a film thickness of 6.33 μm. The coated heat package was dried for at least 30 minutes inside a fume hood. The last traces of solvent were removed in vacuo for 30 minutes prior to vaporization experiments.

After mechanical actuation of the heat package, the aerosol formed by vaporizing the coating in an air flow of 20 L/min at a temperature of greater than 800° C. were collected by passing the air stream containing the aerosol through a PTFE membrane filter (25 mm diameter, 1 μm pore size, Pall Life Sciences) mounted in a Delrin filter (25 mm) holder (Pall Life Sciences). The filter was extracted with 1 ml of acetonitrile (HPLC grade). The filter extract was analyzed by high performance liquid chromatography (HPLC) using a C-18 reverse phase column (4.6 mm ID×150 mm length, 5 μm packing, "Capcell Pak UG120," Shiseido Fine Chemicals, Tokyo, Japan). For pramipexole; a binary mobile phase of eluant A (10 mM $NH_4HCO_3$ in water) and eluant B (10 mM $NH_4HCO_3$ in methanol) was used with a 5-95% linear gradient of B(29 min) at a flow rate of 0.9 mL/min. Detection was at 200-400 nm using a photodiode array detector. Purity was calculated by measuring peak areas from the chromatogram. The purity of the resultant aerosol was determined to be 98.8% with a recovered yield of 95.6%. To increase the purity of the aerosol, one can use lower temperatures for vaporization.

Example 7

Generation of a Ciclesonide Aerosol using Vaporization from a Percussively Ignited Heat Package On an assembled heat package was coated manually a solution of ciclesonide in chloroform using a syringe to apply the coating solution to the end of the heat package containing the fuel (full length of heat package was 1.18 in., drug coated length of the heat package was about 0.39 in). Two to three microliters of solution containing the ciclesonide were applied to coat 0.200 mg of ciclesonide at a film thickness of 2.53 μm. The coated heat package was dried for at least 30 minutes inside a fume hood. The last traces of solvent were removed in vacuo for 30 minutes prior to vaporization experiments.

After mechanical actuation of the heat package, the aerosol formed by vaporizing the coating in an air flow of 20 L/min at a temperature of greater than 800° C. were collected by passing the air stream containing the aerosol through a PTFE membrane filter (25 mm diameter, 1 μm pore size, Pall Life Sciences) mounted in a Delrin filter (25 mm) holder (Pall Life Sciences). The filter was extracted with 1 ml of acetonitrile (HPLC grade). The filter extract was analyzed by high performance liquid chromatography (HPLC) using a C-18 reverse phase column (4.6 mm ID×150 mm length, 5 μm packing, "Capcell Pak UG120," Shiseido Fine Chemicals, Tokyo, Japan). For ciclesonide, a binary mobile phase of eluant A (0.1% trifluoroacetic acid in water) and eluant B (0.1% trifluoroacetic acid in acetonitrile) was used with a 5-95% B linear gradient (24 min) at a flow rate of 1 mL/min. Detection was at 200-400 nm using a photodiode array detector. Purity was calculated by measuring peak areas from the chromatogram. The purity of the resultant aerosol was determined to be 85.6%. To increase the purity of the aerosol, one can use lower temperatures for vaporization Example 8

Firing of Pyrofuze as Fuel using Percussive Ignition

Rather than packing the heat packages with a fuel, the feasibility of using a wire as the fuel was determined.

Various thicknesses of Pyrofuze wire were obtained from Sigmund Cohn. The 0.005 inch thick wire shaped into a U-shape at one end and the gap was filled with a percussive igniter. Upon striking the wire ignited.

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A drug delivery device comprising:
   a housing defining an airway, wherein the airway comprises at least one air inlet and a mouthpiece having at least one air outlet;
   at least one percussively activated heat package disposed within the airway;
   at least one drug disposed on the at least one percussively activated heat package; and
   a mechanism configured to impact the at least one percussively activated heat package.

2. The drug delivery device of claim 1, wherein the percussively activated heat package comprises:
   an enclosure comprising a region capable of being deformed by a mechanical impact;
   an anvil disposed within the enclosure;
   a percussive initiator composition disposed within the enclosure, wherein the initiator composition is configured to be ignited when the deformable region of the enclosure is deformed; and
   a fuel disposed within the enclosure configured to be ignited by the initiator composition.

3. The drug delivery device of claim 1, wherein the drug is disposed on a surface of the heat package as a thin film.

4. The drug delivery device of claim 3, wherein the thickness of the thin film ranges from 0.01 μm to 20 μm.

5. The drug delivery device of claim 3, wherein the thickness of the thin film ranges from 0.5 μm to 10 μm.

6. The drug delivery device of claim 3, wherein the thin film comprises a metal coordination complex of a drug.

7. The drug delivery device of claim 6, wherein the metal coordination complex comprises at least one metal salt and at least one drug.

8. The drug delivery device of claim 7, wherein the at least one metal salt is selected from a salt of Zn, Cu, Fe, Co, Ni, Al, and mixtures thereof.

9. The drug delivery device of claim 6, wherein the thin film comprises a metal coordination complex of zinc bromide and nicotine.

10. The drug delivery device of claim 9, wherein the ratio of zinc bromide to nicotine is about 1:2.

11. The drug delivery device of claim 6, wherein the metal coordination complex is soluble in at least one organic solvent.

12. The drug delivery device of claim 6, wherein the drug is selectively vaporizable from the metal coordination complex when the metal coordination complex comprising the drug is heated to a temperature ranging from 100° C. to 500° C.

13. The drug delivery device of claim 1, wherein the drug is vaporized when heated to a temperature of at least 250° C.

14. The drug delivery device of claim 1, wherein the drug is selected from at least one of the following: albuterol, alprazolam, apomorphine HCl, aripiprazole, atropine, azatadine, benztropine, bromazepam, brompheniramine, budesonide, bumetanide, buprenorphine, butorphanol, carbinoxamine, chlordiazepoxide, chlorpheniramine, ciclesonide, clemastine, clonidine, colchicine, cyproheptadine, diazepam, donepezil, eletriptan, estazolam, estradiol, fentanyl, flumazenil, flunisolide, flunitrazepam, fluphenazine, fluticasone propionate, frovatriptan, galanthamine, granisetron, hydromorphone, hyoscyamine, ibutilide, ketotifen, loperamide, melatonin, metaproterenol, methadone, midazolam, naratriptan, nicotine, oxybutynin, oxycodone, oxymorphone, pergolide, perphenazine, pindolol, pramipexole, prochlorperazine, rizatriptan, ropinirole, scopolamine, selegiline, tadalafil, terbutaline, testosterone, tetrahydrocannabinol, tolterodine, triamcinolone acetonide, triazolam, trifluoperazine, tropisetron, zaleplon, zolmitriptan, and zolpidem.

15. The drug delivery device of claim 1, wherein the drug is selected from the group consisting of nicotine, pramipexole, and a respiratory steroid.

16. The drug delivery device of claim 15, wherein the respiratory steroid is selected from budesonide, ciclesonide, fluisolide, fluticasone propionate, and triamcinolone acetonide.

17. The drug delivery device of claim 1, wherein the mechanism configured to impact is actuated mechanically, electrically, or by inhalation.

18. The drug delivery device of claim 17, wherein the electrical mechanism to impact comprises:
    an airflow sensitive actuator coupled to the airway;
    a mechanism coupled to the airflow sensitive actuator configured to activate the heat package; and
    wherein the heat package is activated by an airflow in the airway produced by inhaling through the mouthpiece.

19. The drug delivery device of claim 17, wherein an inhalation mechanism configured to impact comprises:
    a pressure sensitive diaphragm coupled to the airway;
    a pre-stressed spring disposed within the housing configured to impact the percussively activated heat package when released; and
    a lever rotatably coupled to the diaphragm and the housing, which upon rotation, releases the spring to impact the percussively activated heat package,
    wherein the heat package is activated by an airflow in the airway produced by inhaling through the mouthpiece.

20. The drug delivery device of claim 17, wherein a mechanically actuated mechanism configured to impact comprises:
    a manually operated switch;
    a pre-stressed spring configured to impact the percussively activated heat package; and
    a lever coupled to the switch, which upon actuation, releases the spring to impact the percussively activated heating element.

21. The drug delivery device of claim 17, wherein a mechanically actuated mechanism configured to impact comprises:
    a manually operated switch;
    a mass configured to impact the percussively activated heat package;
    a pre-stressed spring configured to propel the mass;
    a lever coupled to the switch, which upon actuation, releases the spring, propelling the mass to impact the percussively activated heat package.

22. The drug delivery device of claim 21, wherein the at least one drug is selected from nicotine, pramipexole, budesonide, cicliesonide, flunisolide, flutuicasone propionate, and triamcinolone acetonide.

23. The drug delivery device of claim 17, wherein the mechanically actuated mechanism configured to impact comprises a mass configured to impact the percussively activated heat package.

24. The drug delivery device of claim 17, wherein the mechanically actuated mechanism configured to impact comprises a rotatable sleeve that stresses and releases a spring when rotated.

25. The drug delivery device of claim 1, wherein an aerosol comprising the drug is formed in the airway when the heat package is activated.

26. The drug delivery device of claim 25, wherein the vapor purity of the drug forming the aerosol is at least 95%.

27. The drug delivery device of claim 1, wherein an air flow through the airway ranges from 10 L/min to 200 L/min.

28. The drug delivery device of claim 1, wherein the device comprises a plurality of percussively activated heat packages.

29. The drug delivery device of claim 28, wherein each of the plurality of heat packages is disposed within a recess.

30. The drug delivery device of claim 29, wherein the device further comprises a mechanism configured to advance actuation to an unactivated heat package.

31. A drug delivery device comprising:
    a housing defining an airway, wherein the airway comprises at least one air inlet and a mouthpiece having at least one air outlet;
    two or more percussively activated heat packages disposed within the airway;
    at least one drug disposed on the percussively activated heat packages;
    a mechanical mechanism configured to advance actuation to an unactivated heat package; and
    a mechanically actuated mechanism configured to impact the at least one percussively activated heat package.

32. The device of claim 31, wherein the air outlet has a cross sectional area between about 0.01 in$^2$ to 1.5 in$^2$.

33. The device of claim 32, wherein an air flow through the airway ranges from 10 L/min to 200 L/min.

34. The device of claim 31, wherein the device comprises at least five percussively activated heat packages.

35. The device of claim 34, wherein the device comprises at least ten percussively activated heat packages.

36. The drug delivery device of claim 31, wherein each heat package is disposed within a recess.

37. The drug delivery device of claim 31, wherein the mechanically actuated mechanism configured to impact comprises:
    a manually operated switch;
    a pre-stressed spring configured to impact the percussively activated heat package; and
    a lever coupled to the switch, which upon actuation, releases the spring to impact the percussively activated heating element.

38. The drug delivery device of claim 31, wherein the mechanically actuated mechanism configured to impact comprises:
    a manually operated switch;
    a mass configured to impact the percussively activated heat package;
    a pre-stressed spring configured to propel the mass;
    a lever coupled to the switch, which upon actuation, releases the spring, propelling the mass to impact the percussively activated heat package.

39. The drug delivery device of claim 31, wherein the mechanically actuated mechanism configured to impact comprises a mass configured to impact the percussively activated heat package.

40. The drug delivery device of claim 31, wherein the mechanically actuated mechanism configured to impact comprises a rotatable sleeve that stresses and releases a spring when rotated.

41. The drug delivery device of claim 31, wherein the drug disposed on the percussively activated heat packages is disposed as a thin film.

42. The drug delivery device of claim 41, wherein the thin film comprises a metal coordination complex of a drug.

43. The drug delivery device of claim 42, wherein the metal coordination complex comprises at least one metal salt and at least one drug.

44. The drug delivery device of claim 43, wherein the at least one metal salt is selected from a salt of Zn, Cu, Fe, Co, Ni, Al, and mixtures thereof.

45. The drug delivery device of claim 41, wherein the thin film comprises a metal coordination complex of zinc bromide and nicotine.

46. The drug delivery device of claim 45, wherein the ratio of zinc bromide to nicotine is about 1:2.

47. The drug delivery device of claim 31, wherein the at least one drug is selected from at least one of the following: albuterol, alprazolam, apomorphine HCl, aripiprazole, atropine, azatadine, benztropine, bromazepam, brompheniramine, budesonide, bumetanide, buprenorphine, butorphanol, carbinoxamine, chlordiazepoxide, chlorpheniramine, ciclesonide, clemastine, clonidine, colchicine, cyproheptadine, diazepam, donepezil, eletriptan, estazolam, estradiol, fentanyl, flumazenil, flunisolide, flunitrazepam, fluphenazine, fluticasone propionate, frovatriptan, galanthamine, granisetron, hydromorphone, hyoscyamine, ibutilide, ketotifen, loperamide, melatonin, metaproterenol, methadone, midazolam, naratriptan, nicotine, oxybutynin, oxycodone, oxymorphone, pergolide, perphenazine, pindolol, pramipexole, prochlorperazine, rizatriptan, ropinirole, scopolamine, selegiline, tadalafil, terbutaline, testosterone, tetrahydrocannabinol, tolterodine, triamcinolone acetonide, triazolam, trifluoperazine, tropisetron, zaleplon, zolmitriptan, and zolpidem.

48. The drug delivery device of claim 31, wherein the at least one drug is selected from the group consisting of nicotine, pramipexole, and a respiratory steroid.

49. The drug delivery device of claim 48, wherein the respiratory steroid is selected from budesonide, ciclesonide, fluisolide, fluticasone propionate, and triamcinolone acetonide.

50. The drug delivery device of claim 31, wherein the at least one drug is selected from nicotine, pramipexole, budesonide, cicliesonide, flunisolide, flutuicasone propionate, and triamcinolone acetonide.

51. A method of delivering a drug to a patient comprising:
providing a drug delivery device comprising:
a housing defining an airway, wherein the airway comprises at least one air inlet and a mouthpiece having at least one air outlet;
at least two or more percussively activated heat package disposed within the airway;
at least one drug disposed on the at least two or more percussively activated heat package; and
a mechanism configured to impact the percussively activated heat packages;
inhaling through the mouthpiece; and
actuating the mechanism configured to impact;
wherein the percussively activated heat package vaporizes the at least one drug to form an aerosol comprising the drug in the airway which is inhaled by the patient.

52. A drug aerosol delivery device comprising:
a housing defining an airway, wherein the airway comprises at least one air inlet and a mouthpiece comprising at least one air outlet;
a plurality of percussively activated heat packages configured to be disposed within the airway;
a thin film comprising at least one drug disposed on each of the percussively activated heat packages; and
a manually operated switch coupled to at least one spring configured to impact at least one percussively activated heat package disposed within the airway,
wherein when actuated, the drug is vaporized to form an aerosol comprising the drug in the airway.

* * * * *